US009261522B2

(12) United States Patent
Hill et al.

(10) Patent No.: US 9,261,522 B2
(45) Date of Patent: *Feb. 16, 2016

(54) INTEGRITY TESTING OF HAIR SAMPLES

(71) Applicant: Psychemedics Corporation, Acton, MA (US)

(72) Inventors: Virginia Hill, Los Angeles, CA (US); Michael I. Schaffer, Los Angeles, CA (US); Elvan Loni, Torrance, CA (US); Gary Neil Stowe, Manhattan Beach, CA (US)

(73) Assignee: Psychemedics Corporation, Acton, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/664,032

(22) Filed: Mar. 20, 2015

(65) Prior Publication Data
US 2015/0293132 A1 Oct. 15, 2015

Related U.S. Application Data

(63) Continuation of application No. 14/472,252, filed on Aug. 28, 2014, now Pat. No. 8,986,939.

(60) Provisional application No. 61/871,162, filed on Aug. 28, 2013.

(51) Int. Cl.
*G01N 33/94* (2006.01)
(52) U.S. Cl.
CPC .................... *G01N 33/946* (2013.01)
(58) Field of Classification Search
None
See application file for complete search history.

(56) References Cited

U.S. PATENT DOCUMENTS

| 4,956,467 | A | 9/1990 | Hinmann et al. |
| 5,324,642 | A | 6/1994 | Baumgartner |
| 5,350,582 | A | 9/1994 | Merslavic et al. |
| 5,364,642 | A | 11/1994 | Altura et al. |
| 5,466,579 | A | 11/1995 | Baumgartner |
| 5,910,419 | A | 6/1999 | Johnson et al. |
| 5,981,204 | A | 11/1999 | Johnson et al. |

(Continued)

FOREIGN PATENT DOCUMENTS

| EP | 2518474 | 10/2012 |
| WO | WO 03/031935 | 4/2003 |

(Continued)

OTHER PUBLICATIONS

Ahrens et al., "Detection of morphine and monoacetylmophine (MAM) in human hair," J. Anal. Chem., 1992, 344:559-560.

(Continued)

*Primary Examiner* — Jacob Cheu
(74) *Attorney, Agent, or Firm* — Fish & Richardson P.C.

(57) ABSTRACT

Methods for assessing the condition of keratinized structures, including hair, in particular methods to determine the condition of keratinized structures in relation to suitability for analysis of analytes of interest in a test sample, are presented. The methods comprise contacting the keratinized structure with a non-proteolytic reducing agent and an optional proteolytic agent. The methods further include inspection of the hair sample, or measurement of free protein eluted from the keratinized structure, after reduction and optional proteolysis to determine condition prior to analyte identification and quantitation by known techniques such as immunoassays.

24 Claims, 6 Drawing Sheets

(56) References Cited

U.S. PATENT DOCUMENTS

| | | | |
|---|---|---|---|
| 6,022,693 | A | 2/2000 | Baumgartner |
| 6,350,582 | B1 | 2/2002 | Baumgartner |
| 6,537,825 | B1 | 3/2003 | Zollinger et al. |
| 6,949,344 | B1 | 9/2005 | Baumgartner |
| 7,060,453 | B1 | 6/2006 | Fish |
| 7,083,925 | B2 | 8/2006 | Schnabel et al. |
| 7,618,591 | B2 | 11/2009 | Slowey et al. |
| 7,629,129 | B1 | 12/2009 | Sekowski et al. |
| 8,084,215 | B2 | 12/2011 | Hill et al. |
| 8,435,747 | B2 | 5/2013 | Hill et al. |
| 8,501,494 | B1 | 8/2013 | Myagkova et al. |
| 8,986,939 | B1 | 3/2015 | Hill et al. |

FOREIGN PATENT DOCUMENTS

| | | |
|---|---|---|
| WO | WO 2005/039381 | 5/2005 |
| WO | WO 2005/121793 | 12/2005 |
| WO | WO 2009/134852 | 11/2009 |
| WO | WO 2014/005065 | 1/2014 |

OTHER PUBLICATIONS

Albermann et al., "Comparison of ethyl glucuronide (EtG) and fatty acid ethyl esters (FAEEs) concentrations in hair for testing abstinence," Anal. Bioanal Chem, 2011, 400:175-181.

Baptista et al., "Hair analysis for D9-THC, D9-THC-COOH, CBN and CBD, by GC/MS-EI Comparison with GC/MS-NCI for D9-THC-COOH," Forensic Sci. Int., Aug. 2002, 128:68-78.

Baumgartner and Hill, "Hair analysis for drugs of abuse: forensic issues, Proceedings of the International Symposium on Forensic Toxicology," Federal Bureau of Investigation, Jun. 15, 1992, Quantico, 75-97.

Baumgartner and Hill, "Sample Preparation techniques," Forensic Sci Int, 1993, 63:121-135.

Baumgartner et al., "Radioimmunoassay of Hair for Determining Opiate-Abuse Histories," J. Nuclear Med., 1979, 20:748-752.

Baumgartner et al., Forensic Science International, 1993, 63:121-135.

Bradford, "A rapid and sensitive method for the Quantification of Microgram Quantities of Protein Utilizing the Principle of Protein-Dye Binding," Analytical Biochemistry, 1976, 72:248-254.

Cairns et al., "Amphetamines in washed hair of demonstrated users and workplace subjects," Forensic Sci Int., 2004, 145:137-142.

Cairns et al., "Removing and identifying drug contamination in the analysis of human hair," Forensic Sci Int., 2004, 145:97-108.

Cairns et al., Levels of cocaine and its metabolites in washed hair of demonstrated cocaine users and workplace subjects, Forensic Sci Int, 2004, 145:175-181.

Chan et al., "Recent developments in meconium and hair testing methods for the confirmation of gestational exposures to alcohol and tobacco smoke," Clinical Biochemistry, Jun. 2004, 37(6):429-138.

Cooper et al., "Society of Hair Testing guidelines for drug testing hair," Forensic Sci. Int., May 2012, 218(1-3):20-24.

Dolan et al., "An overview of the use of urine, hair, sweat and saliva to detect drug use," Drug and Alcohol Review, 2004, 23(2):213-217.

Gratacos-Cubarsi et al., "Hair analysis for veterinary drug monitoring in livestock production," Journal of Chromatography B., 2006, 834:14-25.

Gratacos-Cubarsi et al., J. Chromatography B, 2006, 832:121-126.

Han et al., "A simple improved method for protein extraction from human head hairs," J. Cosmet Sci., Sep./Oct. 2007, 58:527-534.

Harrison and Fu, "A Review of Methodology for Testing Hair for Cocaine," J. Forensic Sci., Jan. 2014, vol. 2(1):1-8.

Hessefort et al., J. Cosmet. Sci., 2008, 59:303-315.

Hill et al., "Hair analysis for cocaine: Factors in laboratory contamination studies and their relevance to proficiency sample preparation and hair testing practices," Forensic Sci Intern., 2008, 176:23-33.

Inoue et al., "Elution of 8100A3 from hair fiber: New model for hair damage emphasizing the loss S100A3 from cuticle," J. Cosmet. Sci., Jan./Feb. 2000, 51:15-25.

Inoue et al., "Labile proteins accumulated in damaged hair upon permanent waving and bleaching treatments," J. Cosmet Sci., Nov./Dec. 2002, 53:337-344.

Jeong et al., "Hair Damage and Wave Efficiency according to the Degree of Alkalinity in Permanent Wave," Applied Microscopy, 2012, 42(3):136-141.

Juardo et al., "Influence of the cosmetic treatment of hair on drug testing," Int. J. Legal Med., 1997, 110:159-163.

Kintz et al., "Simultaneous determination of amphetamine, methamphetamine, 3,4-methylenedioxyamphetamine and 3,4-methylenedioxymethamphetamine in human hair by gas chromatography-mass spectrometry," J. Chromatography B: Biomedical Sciences and Applications, Aug. 1995, 670(1):162-166.

Kintz et al., "Testing for the undetectable in drug-facilitated sexual assault using hair analyzed by tandem mass spectrometry as evidence," Therapeutic Drug Monitoring, Apr. 2004, 26(2):211-214.

Kintz et al., "Testing human hair for cannabis. II. Identification of THC-COOH by GC-MS-NCI as a unique proof," J. Forensic Sci., Jul. 1995, 40(4):619-622.

Kintz, "Testing for anabolic steroids in hair: a review," Legal Medicine, Mar. 2003, 5(Supplement): S29-S33.

Koster et al., "Fast and highly selective LC-MS/MS screening for THC and 16 other abused drugs and metabolites in human hair to monitor patients for drug abuse," Therapeutic Drug Monitoring, Apr. 2014, 36(2):234-243.

Kronstad et al., "A screening method for 30 drugs in hair using ultrahigh-performance liquid chromatography time-of-flight mass spectrometry," Therapeutic Drug Monitoring, Jun. 2013, 35(3):288-295.

Kuzuhara, "A new method of internal structural analysis of keratin fibers using Raman spectroscopy," Biopolymer Res Trends, 2007, 49.

Yegels et al., "Detection of benzodiazepines and other psychotropic drugs in human hair by GC/MS," Forensic Sci. Int., Jan. 1997, 84(1-3):211-218.

Lopez-Guarnido et al., "Hair testing for cocaine and metabolites by GC/MS: criteria to quantitatively assess cocaine use," J. Applied Toxicology, Aug. 2013, 33(8):838-844.

Lowry et al., "Protein measurement with the folin phenol reagent," J. Biol. Chem., 1951, 193:265-275.

Martins et al., "Influence of bleaching on the enantiomeric disposition of amphetamine-type stimulants in hair," Forensic Sci. Intern., 2008, 176:38-41.

Mathematik, "Damage assessment of human hair by electrophoretical analysis of hair protein," Ph.D Thesis, available online, 2004.

Mussoff and Madea, "Analytical pitfalls in hair testing," Anal Bioanal Chem, 2007, 388:1475-1494.

Nielen et al., "Multi residue screening of intact testosterone esters and boldenone undecylenate in bovine hair using liquid chromatography electrospray tandem mass spectrometry," J. Chromatography B., 2006, 830:126-134.

Polettini et al., "Determination of opiates in hair. Effects of extraction methods on recovery and on stability of analytes," Forensic Sci. Int., Jan. 1997, 84(1-3):259-269.

Polettini et al., "Incorporation of methamphetamine and amphetamine in human hair following controlled oral methamphetamine administration," Anal. Chim. Act., 2012, 726:35-43.

Potsch et al., "Stability of opiates in hair fibers after exposure to cosmetic treatment," Forensic Sci Inter., 1996, 81:95-102.

Robbins, Chemical and Physical Behavior of Hair, Springer, New York, 2002, 434-436.

Robbins, Chemical and Physical Behavior of Hair, Springer, New York, 2002, 256-261.

Robbins, Chemical and Physical Behavior of Hair, Springer, New York, 2002, 441-446.

Roe et al., "The detection of cosmetic treatments on human scalp hair. Screening of forensic samples," Proceedings of the International Symposium on Forensic Hair Comparisons, Washington DC, 1985, 63-68.

Ropero-Miller and Stout, "Analysis of cocaine analytes in human hair. II. Evaluation of Different Hair Color and ethnicity types," Reports to the US Department of Justice, Document 234628, Jun. 2011, 235 pages.

(56) References Cited

OTHER PUBLICATIONS

Schaffer et al., "An Evaluation of Two Wash Procedures for the Differentiation of External Contamination versus Ingestion in the Analysis of Human Hair Samples for Cocaine," J. Anal Toxicol., 2002, 26:485-488.

Schaffer et al., "Hair Analysis for Cocaine: The requirement for Effective Wash Procedures and Effects of Drug Concentration and Hair Porosity in Contamination and Decontamination," J. Anal Toxicol., 2005, 29:319-326.

Sinclair et al., "The proteomic profile of hair damage," British Assoc. of Dermatologists, 2012, 166(2):27-32.

Skopp et al., "On cosmetically treated hair—aspects and pitfalls of interpretation," Forensic Sci Intern., 1997, 84:43-52.

Stout et al., "External contamination of hair with cocaine: Evaluation of external cocaine contamination and development of performance-testing materials," J. Anal Tox., 2006, 30:490-496.

Takayama et al., "High-performance liquid chromatography study on effects of permanent wave, dye and decolorant treatments on methamphetamine and amphetamine in hair," Biomedical Chromatography, 1999, 13:257-261.

Tanaka et al., "Analysis of reaction products of cocaine and hydrogen peroxide by high performance liquid chromatography/mass spectrometry," Biomedical Chromatography, 2002, 16:390-394.

Tanaka et al., "Identification of reaction products of methamphetamine and hydrogen peroxide in hair dye and decolorant treatments by high-performance liquid chromatography/mass spectrometry," Biomedical Chromatography, 2001, 15:45-49.

Tate et al., "Quantification and Prevention of hair damage," J. Cosmet Sci., Nov./Dec. 1993, 44:347-371.

Tsanaclis and Wicks, "Differentiation between drug use and environmental contamination when testing for drugs in hair," Forensic Sci Int., 2008, 145:97-108.

Villain et al., "Testing for zopiclone in hair application to drug-facilitated crimes," Forensic Sci Int., Oct. 2004, 145(2-3):117-121.

Vincenti et al., "Role of LC-MS/MS in hair testing for the determination of common drugs of abuse and other psychoactive drugs," Bioanalysis, Aug. 2013, 5(15):1919-1938.

Yegles et al., "Influence of bleaching on stability of benzodiazepines in hair," Forensic Sci. Intern., 2000, 107:87-92.

Yegles, "Pitfalls in hair analysis: cosmetic treatment," Annales de Toxicologic Analytique, 2005, 17:275-278 (with English Abstract).

Zor et al., "Linearization of the Bradford Protein Assay Increases Its Sensitivity: Theoretical and Experimental Studies," Analytical Biochemistry, 1996, 236:302-308, Article No. 0171.

Davis et al., "Utilizing Proteomics to characterize Hair and Hair Damage at the Molecular Level," P&G Beauty and Grooming, presented on Sep. 30, 2011, 14 pages.

Hill et al., "Identification and analysis of damaged or porous hair," Drug Testing and Analysis, May 2014, 6:42-54.

International Search Report and Written Opinion in International Application No. PCT/US2014/053261, dated Jul. 14, 2015, 16 pages.

75 minutes 90 minutes

INTEGRITY TESTING OF HAIR SAMPLES

CROSS-REFERENCE TO RELATED APPLICATIONS

This application is a continuation of U.S. application Ser. No. 14/472,252, filed Aug. 28, 2014, which claims priority to U.S. Provisional Application Ser. No. 61/871,162, filed on Aug. 28, 2013.

TECHNICAL FIELD

This disclosure relates to methods for assessing the condition of keratinized structures (e.g., hair), in particular assessing the degree of damage in the hair. This disclosure also relates to methods for determining the presence or quantitation of analyte(s) of interest in keratinized structures, particularly hair, in particular to methods for assessing the hair condition to determine the appropriate analytic process for a particular sample, or to determine whether a sample has been subjected to procedures or conditions to render it invalid for accurate analyte analysis.

BACKGROUND

The analysis of keratinized structures, particularly hair, for the identification and quantitation of ingested analytes is a well established practice (U.S. Pat. No. 5,364,642, U.S. Pat. No. 8,084,215). An important concern for hair analyte analysis is the change in hair condition induced by cosmetic treatment (e.g., bleaching, highlights, coloring or perms), heat treatment (e.g. heat of dryers, curling irons or flat irons) or other sources such as combing, humidity, dryness, dirt, sunrays (UV and infared radiation) and pollution in the atmosphere. However, hair damage occurs mostly in the form of physical and chemical changes as a result of bleaching, oxidative dyeing, hair relaxing via alkaline relaxers, reducing waving and curling preparation. In addition to the cosmetic treatments named above, hair can also exhibit damage from mechanical actions such as excessive brushing, rubber-banding (e.g., ponytails), [12] or constant friction (e.g. body hair against clothing). While chemical interactions between the cosmetic agents and the analytes themselves are one aspect of such cosmetic treatments, an effect common to all is damage to the hair, especially disruption of the cuticular sheath resulting in increased porosity of the hair.

Increased porosity of the hair affects two main aspects of hair analysis: (1) contaminants entering the hair and (2) compounds present from ingestion being lost from the hair. Regarding the first aspect, contaminants such as drugs diffuse into the hair as solutes in solvents, particularly hair-swelling solvents; water, which swells normal intact hair about 14-16% within 30 minutes is the most prevalent and likely solvent involved in real-life contamination. Porous hair can absorb 10-20 times as much drug as intact hair under the same exposure conditions. The second aspect of the effects of porosity in hair analysis, the loss of drugs from ingestion due to cosmetic damage, is very much a function of the degree of porosity caused by the cosmetic damage. If the porosity is extremely severe, which can result from applying cosmetic treatments in degrees not recommended by the cosmetic industry, drug may be lost from the sample even before the sample reaches the laboratory. Thus, there is a need to identify such samples as too damaged to produce a reliable result as to drug ingestion and reported accordingly.

The assessment of hair damage as a result of the aforementioned variables is desired to provide reproducible and reliable methods for determining the presence of targeted analytes in hair samples. Hair damage has been previously measured by a variety of methods including microfluorometry, colorimetric staining, microscopy, scanning electron microscopy and Wilhelmy wettability. These methods, while effective, suffer from their time-consuming and laborious nature. For example, hair damage can be determined by Methylene Blue staining (For Sci Int 176 (2008) 23-33), but the method requires staining and slide mounting of many individual samples, making it incompatible with high volume hair analyte analysis. Thus, a need exists for more rapid, high-throughput protocols that are amenable to the screening of high quantities of hair samples commonly found in hair analysis laboratories.

SUMMARY

This invention is based, in part, on the discovery that the amount of target analyte(s) retained within a keratinized structure, particularly a hair sample, may change based upon the condition of the hair sample, thus influencing the detection and quantitation of the target analyte(s). The invention is also based, in part, on the discovery that hair sample condition may affect the choice of hair washing methods to remove external/environmental contamination to distinguish presence of analyte(s) due to contamination from analyte(s) present by ingestion.

The present invention provides rapid and reliable methods for determining the condition of keratinized structures, particularly hair, as it relates to the analysis of analyte(s) released from these structures following proteolytic or non-proteolytic digestion. Accordingly, in one aspect, the invention features methods for optimizing methods for the analysis of analytes from hair samples of an individual (who may have been exposed (e.g., ingestion, inhalation, or injection) to one or more analytes).

In one aspect, the disclosure provides methods for determining the presence or absence of a drug of abuse or metabolite thereof in a hair sample of a subject comprising: providing a hair sample from the subject; contacting the hair sample with an aqueous solution comprising a reducing agent to result in a test sample; subjecting the aqueous portion of the test sample to denaturing conditions; measuring the absorption of the subjected aqueous solution to determine if the sample is suitable for further processing; and determining if an analyte is present or absent in a hair sample identified as suitable for further processing.

In another aspect, the disclosure provides methods for determining the presence or absence of a drug of abuse or metabolite thereof in a hair sample comprising: providing a hair sample from a subject; determining if the hair sample is not suitable for drug analyte testing comprising: contacting the hair sample with an aqueous solution comprising a reducing agent to result in a test sample; and identifying the hair in the test sample as not suitable for drug analyte testing when the hair in the test sample has dissolved in the test sample more rapidly than the hair in a similarly contacted control sample or the hair in the test sample appears softer or less rigid as compared to the hair in the similarly contacted control sample; and if the hair in the test sample is not identified as not suitable for drug analyte testing, then determine if the drug of abuse is present or absent in the hair sample.

In yet another aspect, the disclosure provides methods for determining the presence or absence of a drug of abuse or metabolite thereof in a hair sample of a subject comprising: providing a hair sample; determining if the hair sample is not suitable for drug analyte testing comprising: contacting the hair sample with an aqueous solution comprising a reducing agent and a protease capable of digesting keratin to result in a test sample; identifying the hair in the test sample as not suitable for drug analyte testing when the hair in the test sample has dissolved in the test sample more rapidly than the hair in a similarly contacted control sample or the hair in the test sample appears softer or less rigid as compared to the hair in the similarly contacted control sample; and if the hair in the test sample is not identified as not suitable for drug analyte testing, then determine if the drug of abuse is present or absent in the hair sample.

Also provided herein are methods for determining the presence of an analyte in a hair sample of a subject, the methods comprising: assessing the condition of a hair sample; and determining if the analyte is present in the hair sample.

The hair sample condition assessment step can be completed using an aliquot of the same portion of sample that will be analyzed for analytes by methods, including, for example, such as an immunoassay, a mass spectrometry technique or a chromatographic technique. The hair sample condition assessment step can also be completed using a first portion of the hair sample, and a second portion of the same sample used for identification and quantitation of the analyte(s). In one aspect, the step of assessing the condition of the hair sample comprises providing a hair sample; contacting the hair sample with an aqueous solution comprising a reducing agent to result in a test sample; comparing the condition of the hair in the test sample to a control sample; and identifying the hair sample as damaged when the hair sample has dissolved in the test solution more rapidly than the control sample, or the hair sample appears soft and less rigid as compared to the control sample, or identifying the hair sample as suitable for further processing if the condition of the hair in the test solution is commensurate with the condition of the control sample.

In some embodiments, the methods provided herein further comprising purifying the test sample to separate the residual keratinized sample from the test solution, wherein the purification does not proteolytically cleave the keratinized structure, to result in a purified test solution, and determining if the analyte is present in the purified test solution.

In some embodiments of the non-proteolytic methods described herein, the methods further comprise deactivating residual reducing agent present in the test solution prior to the determining step, to result in a deactivated test solution. The agent used form the deactivating step may be any agent suitable deactivating residual reducing agent, as long as the deactivating agent does not proteolytically cleave the keratinized structure. In one embodiment, the deactivation step comprises contacting the test solution with an aqueous solution of a metal salt, wherein the metal cation of the salt is selected from the group consisting of Cu++, Zn++, Mn++, Fe+++, Fe++, Pb++, Cd++, Hg++, Ag++, As+++, and Co++.

In another aspect, the step of assessing the condition of the hair sample comprises contacting the sample with an aqueous solution of non-proteolytic reducing agent to result in a test sample, comparing the test sample with a control sample, and identifying the test sample as damaged for analyte analysis when the hair sample has dissolved, appears soft, or is less rigid in comparison to the control sample.

In yet another aspect, the step of assessing the condition of the hair sample comprises contacting the sample with an aqueous solution of non-proteolytic reducing agent to result in a test sample, measuring protein eluted from the sample using established techniques (Lowry, Bradford assay), comparing protein eluted from the test sample with a control sample, and identifying the test sample as damaged for analyte analysis when protein has eluted from the test sample.

In some embodiments, the step assessing the condition of the hair sample comprises providing a hair sample; contacting the hair sample with an aqueous solution comprising a reducing agent to result in a test sample; denaturing the protein in the test sample; estimating the degree of damage to hair by absorption spectrophotometry of the test sample after protein denaturation to identify hair samples suitable for further processing; and selecting methods for determining an analyte is present in a hair sample based on the condition of the hair.

In some embodiments, the step assessing the condition of the hair sample comprises providing a hair sample; contacting the hair sample with an aqueous solution comprising a reducing agent to result in a test sample; denaturing the protein in the test sample; estimating the degree of damage to hair in the test sample by absorption spectrophotometry to identify hair samples suitable for further processing; and determining if an analyte is present in a hair sample identified as suitable for further processing.

Evaluating the degree of damage to the hair can be accomplished by absorption spectrophotometry at a wavelength of 190 nm ($A_{190}$) to 380 nm ($A_{380}$) (e.g., $A_{190}$, $A_{200}$, $A_{240}$, $A_{280}$, $A_{300}$, $A_{340}$ or $A_{380}$). In one embodiment, evaluating the degree of damage to the hair is performed by absorption spectrophotometry at a wavelength of 380 nm ($A_{380}$). For methods performed by absorption spectrophotometry at a wavelength of 380 nm ($A_{380}$), samples having $A_{380}$ value above a threshold value (e.g., 0.35 or greater) can be identified as not being suitable for further processing (e.g., not being suitable for use in determining if an analyte is present in the hair sample). Conversely, samples having $A_{380}$ value below a threshold value (e.g., 0.35 or less) can be identified as being suitable for further processing (e.g., suitable for use in determining if an analyte is present in the hair sample).

In some embodiments, the denaturing step comprises adjusting the pH of the test sample to a pH of 4.0 or less, 3.5 or less, 3.0 or less, or 2.0 or less.

In some embodiments, the denaturing step comprises adding an organic solvent to the test sample. Exemplary organic solvents for use in the denaturing step include, for example, an organic solvent selected from the group consisting of methanol, ethanol, propanol, 2-propanol, acetone, acetonitrile, and mixtures thereof. In another embodiments, the denaturing step comprises adding trichloroacetic acid (e.g., 2,2,2-Trichloroacetic acid trichloroacetic acid, acetic acid, or sulfosalicyc acid to the test sample. In some embodiments, the denaturing step comprises subjecting the hair sample to high heat or high acid. In some embodiments, the non-proteolytic reducing agent is selected from the group consisting of 2,3 dihydroxybutane-1,4-dithiol ("DTT"), 2,3 dihydroxybutane-1,4-dithiol ("DTE"), thioglycolate, cysteine, sulfites, bisulfites, sulfides, bisulfides, tris(2-carboxyethyl) phosphine ("TCEP"), or mixtures thereof. For example, the non-proteolytic reducing agent can be DTT or DTE. In some embodiments, the aqueous solution comprises 0.1%, 0.2%, 0.3%, 0.4%, 0.5%, 0.6%, 0.7%, 0.8%, 0.9%, 1.0%, 1.5%, 2.0%, 2.5% or 3.0% of the reducing agent.

The pH at which the contacting step or the determining step can be performed is between about 7.0 and 10.5, between about 8.8 and 10.5, between about 8.8 and 9.7, between about 8.8 and 9.5, or between about 9.4 and 9.7.

In one aspect, the temperature at which the contacting step or the determining step can be performed is between about 20° C. and about 40° C.; and for a time period of about 0.5 hours to 12 hours. In one embodiment, the contacting step occurs for a time period of about 1.5 hours to about 2 hours.

In one aspect, modification of the test sample to denature protein comprises adjustment of pH by addition of acid to a value of approximately 2. In another aspect, organic solvents such as methanol, ethanol and acetonitrile are added denature protein.

In one aspect, the step of assessing the condition of the hair sample comprises contacting the sample with an aqueous solution of non-proteolytic reducing agent and a protease suitable for digestion of keratin, comparing the test sample to a control sample, and identifying the hair sample as damaged for analyte analysis when the sample has dissolved in the test solution or the hair sample appears soft and less rigid as compared to the control.

In another aspect, the step of assessing the condition of the hair sample comprises contacting the sample with an aqueous solution of non-proteolytic reducing agent and a protease suitable for digestion of keratin, comparing the test sample to a control sample, and identifying the hair sample as suitable for analyte analysis when the hair sample appears similar to the control.

In some embodiments, the step of assessing the condition of the hair sample comprises providing a hair sample; contacting the hair sample with an aqueous solution comprising a reducing agent and a protease capable of digesting keratin to result in a test sample; comparing the condition of the hair in the test sample to a control sample; and identifying the hair sample as damaged when the hair sample has dissolved more rapidly in the test solution than the control sample, or the hair sample appears soft and less rigid as compared to the control sample, or identifying the hair sample as suitable for further processing if the rate of dissolution in the test solution is commensurate with the rate of dissolution in the control sample. In some embodiments, the condition of the hair is determined based on degree of dissolution of the hair in the test solution.

In one aspect, the condition of the test sample in proteolytic solution is determined by one or more factors selected from the group consisting of softness, rigidity and degree of dissolution/disintegration. In one embodiment, the condition of the sample for analyte analysis is assessed by visual inspection.

In one aspect, the protease is selected from the group consisting of papain, chymopapain and proteinase K.

For the proteolytic methods disclosed herein, hair sample condition is assessed by visual inspection at predetermined time intervals following the contacting step. In one embodiment, the predetermined time intervals are about 10 minute, about 15 minute, about 20 minute and about 30 minute intervals. The hair sample degree of damage corresponds to hair sample dissolution speed; this information can be used to determine appropriate alternate wash procedures applicable to the sample to discern external/environmental analyte contamination from analyte ingestion.

In some embodiments, the proteolytic methods disclosed herein further comprise identifying the hair sample as being previously treated with a cellophane hair treatment if a dye is visible in the test solution within about 5 minutes of contacting the hair sample with an aqueous solution comprising a reducing agent and a protease. In other embodiments the proteolytic methods disclosed herein, further comprise identifying the hair sample as being previously treated with potassium hydroxide if the hair sample fails to dissolve after a time period of about 120 minutes.

In yet another embodiment, the proteolytic methods disclosed herein further comprise identifying the hair sample as being previously treated with a cellophane hair treatment if a dye is visible in the test solution within about 5 minutes of contacting the hair sample with an aqueous solution comprising a reducing agent and a protease.

The step of determining whether an analyte is present or not present can be performed using an enzyme immunoassay specific for the analyte (e.g., using an antibody specific for the analyte), using a mass spectrometry technique, or using a chromatographic technique.

In some aspects, the determining step comprises (a) providing an optionally washed hair sample; (b) contacting the hair sample with an aqueous solution of a reducing agent to result in a test solution; and (c) determining if the analyte is present in the test solution.

In some embodiments, the method further comprises determining the amount of analyte present, if the analyte is present. For example, the amount of the analyte present can be determined quantitatively.

The analyte to be detected can be a drug of abuse or metabolite thereof, a prescription medicine or metabolite thereof, a pain medication or metabolite thereof, a nutrient, or an endogenous analyte, or a salt form of any of the foregoing. For example, the drug of abuse or metabolite thereof is selected from the group consisting of: cocaine, benzoylecgonine, cocaethylene, norcocaine, PCP, amphetamine, methamphetamine, cannabinoid, THC, carboxy-THC, heroin, codeine, morphine, 6-acetylmorphine (6-MAM), oxycodone, 3,4-methylenedioxyamphetamine (MDA); and 3,4 methylenedioxymethamphetamine (MDMA). The drug of abuse of metabolite thereof, prescription medicine or metabolite thereof, or pain medication or metabolite thereof, including, for example, an opioid, cannabinoid, NSAID, steroid, amphetamine, benzodiazepine, barbiturate, tricyclic, or ephedrine or metabolite thereof.

The analyte to be detected can be a trace metal selected from the group consisting of iron, magnesium, lithium, zinc, copper, chromium, nickel, cobalt, vanadium, arsenic, molybdenum, manganese and selenium.

In some embodiments, the methods disclosed herein further comprise indicating the hair sample as unsuitable for determining if the analyte is present in the test solution when the hair sample has been identified as damaged. For hair samples identified as damaged, the methods can further comprise requesting a new hair sample from the subject.

Unless otherwise defined, all technical and scientific terms used herein have the same meaning as commonly understood by one of ordinary skill in the art to which this disclosure pertains. Although methods and materials similar or equivalent to those described herein can be used in the practice or testing of the presently described methods, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages will be apparent from the following detailed description, and from the claims.

DETAILED DESCRIPTION

Figure 1:
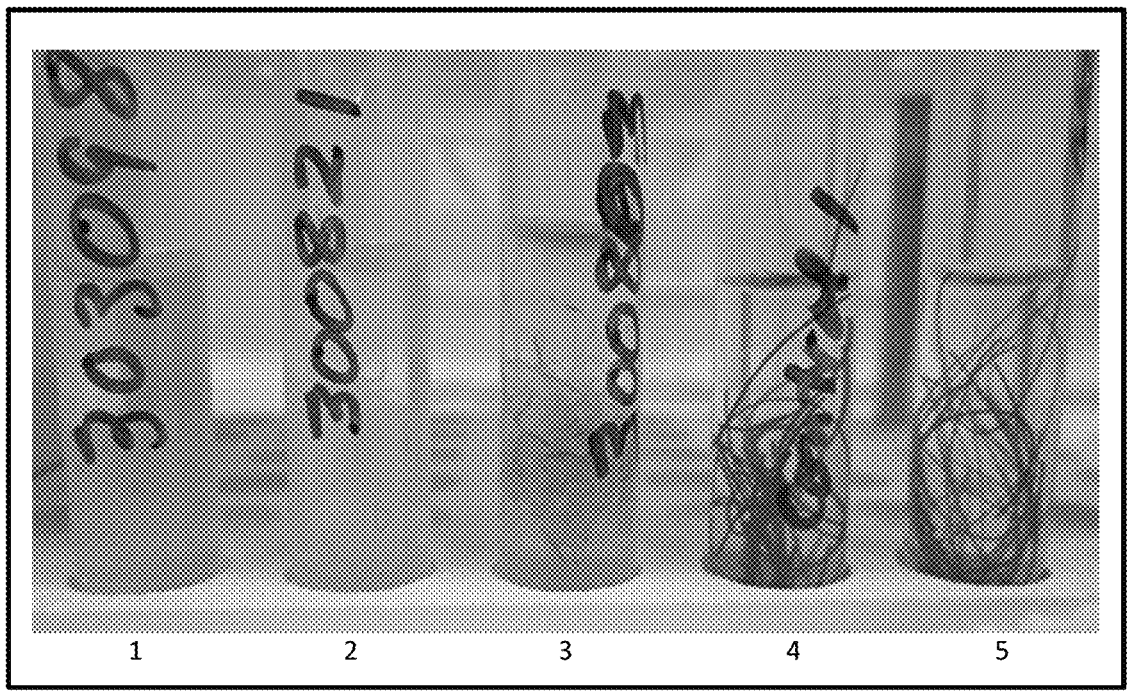
FIG. 1 is a photograph demonstrating hair samples following treatment with a reducing agent.
Figure 2A:
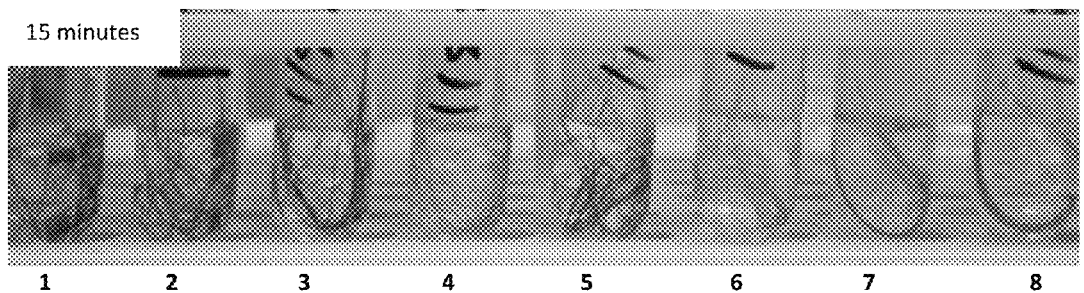
FIGS. 2A-2F are a series of photographs demonstrating hair samples at 15, 30, 45, 60, 75 and 90 minutes following treatment using a proteolytic digestion.
Figure 2B:
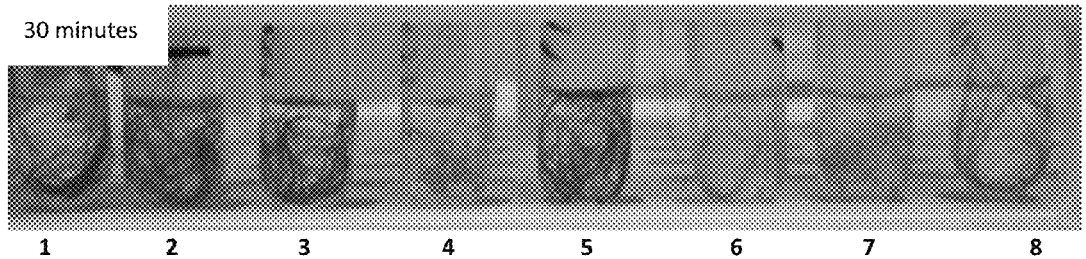
Figure 2C:
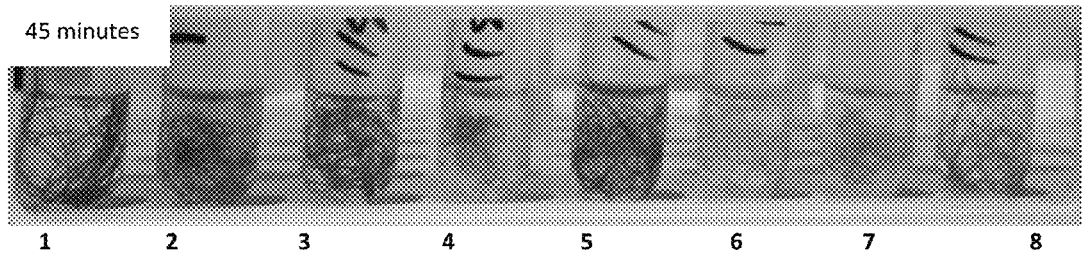
Figure 2D:
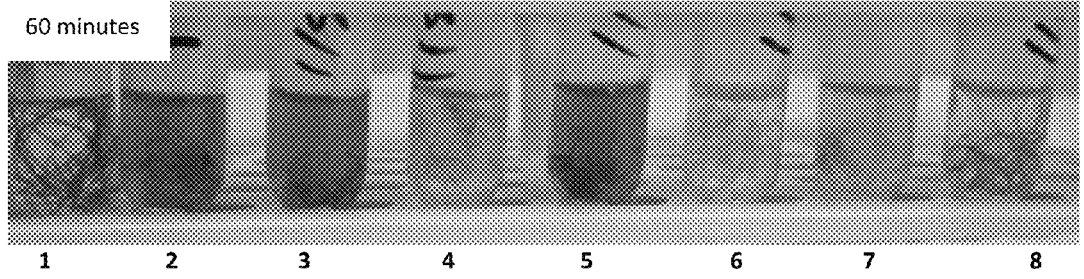
Figure 2E:
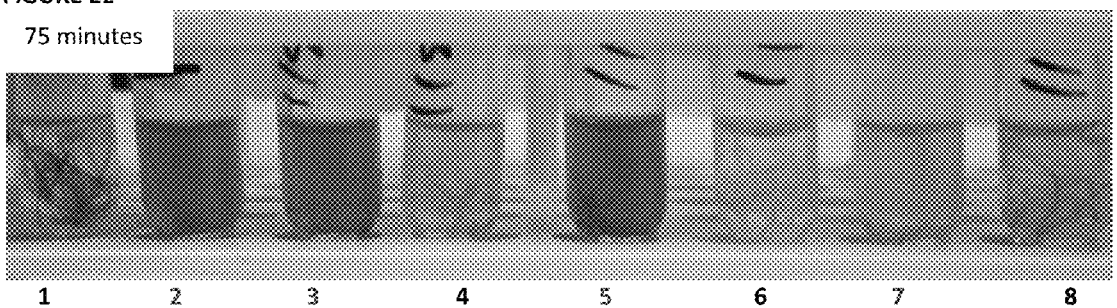
Figure 2F:
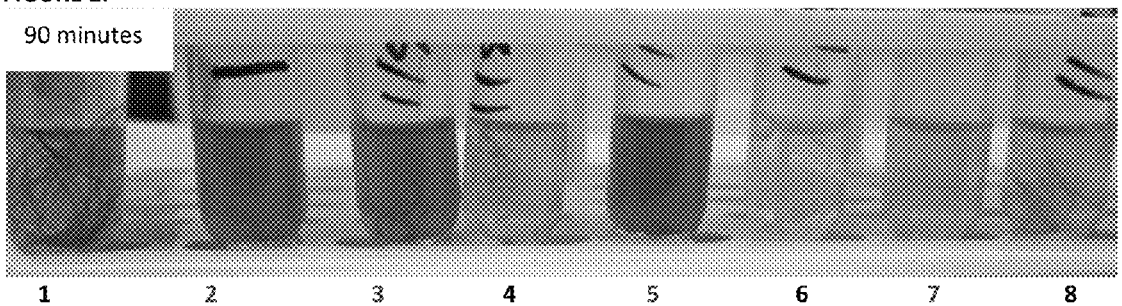

In accordance with the present invention, methods are provided for evaluating the condition, also termed integrity, of a hair sample being tested for analyte(s) of interest. The methods provided herein permit hair sample characterization to evaluate if the hair sample is intact (of high integrity), and suitable for analyte testing, or if the sample has been sufficiently damaged (of low integrity) to make it unsuitable for analyte testing.

Accordingly, provided herein are methods for determining the presence of an analyte in a keratinized structure of a subject, the methods comprising: assessing the condition of a keratinized structure sample; and determining if the analyte is present in the keratinized structure sample. In some embodiments, the keratinized structure is hair. Thus, provided herein are methods for determining the presence of an analyte in a hair sample of a subject, the methods comprising: assessing the condition of a hair sample; and determining if the analyte is present in the hair sample.

In some embodiments, the hair is washed repeatedly, e.g., two, three, four, five, six, seven, eight, or more times. Hair washing can be performed by any suitable method as is known by those of skill in the art, including without limitation using a method as described in, e.g., Baumgartner and Hill, Sample Preparation Techniques, Forensic Science Int. 63 (1993) 121-135. A hair sample can be washed in any appropriate buffer, including, for example, about 0.005 M to about 0.2 M phosphate buffer (e.g., about 0.075 M, 0.01 M, 0.02 M, 0.03 M, 0.04 M, 0.05 M, 0.06 M, 0.07 M, 0.08 M, 0.09 M, 0.1 M, 0.15 M, 0.175 M) at a pH of from about 4.5 to about 10.5 (e.g., about 4.5 to about 6.5; about 5.5 to about 6.5; about 5.7 to about 6.2; about 5.9 to about 6.1; about 5.8 to about 7.5; about 5.8 to about 8; about 6 to about 9; about 5.5 to about 9.5; about 5.8, about 6.0, about 6.1, about 6.2, about 6.3, about 6.4, about 6.5, about 6.6, about 6.7, about 6.8, about 6.9, or about 7.0 pH). In some embodiments, the hair is washed in about 0.01 M phosphate buffer about pH 6.0. The hair can be washed in the suitable buffer at a temperature of about 25 to about 45° C., e.g., about 25 to about 32; about 28 to about 32; about 30 to about 40; about 25 to about 35° C.

In these methods, a hair sample is first collected from a subject, e.g., a subject who may have been exposed to a particular analyte or is suspected of having been so. As used herein, the term "analyte" refers to any compound, whether endogenously produced or exogenously introduced in a subject.

Thus, in some embodiments, an analyte of interest can be exogenously introduced in the subject, i.e., not normally present in the subject, but introduced through an exogenous method, such as via inhalation, parenteral administration (e.g., IV, transdermal, subcutaneous, or IM routes), or ingestion (e.g., oral, buccal, or transmucosal routes). As used herein, a metabolite or degradation product of an exogenously introduced analyte is an exogenous analyte of interest, despite the fact that it is endogenously made in vivo in a subject, because it was derived from an exogenously introduced analyte.

As used herein, the phrases "determine the presence" and "determining the presence" mean determining whether or not an analyte is present. Thus, if an analyte is determined to be absent, such an activity would still be encompassed by the phrases.

As used herein, a hair sample in test sample "dissolves" or "has dissolved" "more rapidly" than another hair sample (e.g., a control sample) when the hair sample in test sample dissolves in about 5% to about 95%, e.g., about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, or about 95%, of the time it takes for the hair in the control sample to dissolve.

The terms "control hair sample" or "hair in a control sample" and the like are used interchangeably and refer to untreated hair (e.g., hair samples with no prior cosmetic treatments) or hair samples previously determined as not being excessively damages or porous.

An analyte can be any chemical, including drugs of abuse, toxic chemicals, environmental chemicals (e.g., pesticides, herbicides, insecticides), petroleum products, natural products, organic compounds, nutrients, prescription or over-the-counter medications (e.g., pain medications, steroids, narcotics, NSAIDS), or metabolites, derivatives, or breakdown products of any of the foregoing.

In some embodiments, an analyte of interest can be an exogenously introduced drug-of abuse, prescription medication, pain medication, organic compound, nutrient, metal, toxic chemical, pesticide, or a metabolite or degradation product thereof. Examples of drugs of abuse, pain medications, or prescription medications, or metabolites thereof, include an opioid, cannabinoid, NSAID, steroid, amphetamine, benzodiazepine, barbiturate, tricyclic, or ephedrine, or metabolite thereof.

Specific examples include: cocaine (and metabolites benzoylecgonine, cocaethylene, and norcocaine), opioids and metabolites thereof (morphine, heroin, 6-monoacetylmorphine, diacetylmorphine, codeine, oxycodone, hydrocodone, hydromorphone, oxymorphone, and methadone), cannabinoids, phencyclidine (PCP), amphetamines, methamphetamines, MDMA (ecstasy, methylenedioxy methamphetamine), MDA (methylenedioxyamphetamine), marijuana (and THC and carboxy-THC metabolites), propoxyphene, meperidine, benzodiazepines, carisoprodol, tramadol, fentanyl, buprenorphine, naltrexone, tricyclics, nicotine (and its metabolite cotinine), eve (methylenedioxy-ethylamphetamine), flunitrazepam, lysergic acid (LSD), digoxin, methylphenidate, acetaminophen, salicylates, fluoxetine, sertraline, dextromethorphan, ephedrine, phenethylamines, pseudoephedrine, and synephrine. Pesticides include, without limitation, parathion, malathion, chlorpyrifos, diazinon, dichlorvos, and tetrachlorvinphos.

In other embodiments, an analyte of interest is endogenously produced, e.g., in an amount that correlates with the presence or absence of a disease state or metabolic state of a subject. Examples of endogenous analytes include fatty acid esters (e.g., as markers of alcohol consumption); chromium (e.g., as measure of glucose tolerance and type 2 diabetes); glucose (e.g., as measure of glucose tolerance and type 2 diabetes); and glycosyl groups (e.g., as a measure of chronic hyperglycaemia).

In one aspect, a hair sample is first collected from a subject suspected of having been exposed to, or having ingested, a particular analyte. Preferably, the hair sample is first washed by known methods to remove analyte or other drug or chemical which may have been deposited on the surface of the hair by external contact rather than by actual consumption. The sample is then subjected to proteolytic or non-proteolytic digestion methods, so as to effectuate trapped analyte release.

In one aspect, the hair sample is subjected to non-proteolytic methods to release entrapped analytes. For the non-proteolytic digestion methods, treatment of the hair sample does not include contacting the hair sample with one or more proteolytic enzymes, such as papain, chymopapain, and proteinase K. Thus, the treatment method does not proteolytically cleave peptide (amide) bonds in the structure, e.g., not cleave them substantially. In some embodiments, the method reduces, e.g., reduces substantially, disulfide bonds present in the hair sample but does not cleave peptide bonds (e.g., does not cleave them substantially) in the sample. Typically, the treatment method comprises a reducing step, an optional deactivation step, and an optional purification (e.g., separation, filtration, or centrifugation) step.

In the non-proteolytic reducing step, the sample is contacted with a solution of a reducing agent (reducing solution), such as Dithiothreitol ("DTT"), so as to reduce inter- and intra-molecular disulfide bonds in the keratin macrostructure, thereby releasing entrapped analyte. In some embodiments the keratinized structure sample can be contacted with a non-proteolytic reducing solution consisting essentially of the reducing agent, or can be contacted with a reducing solution that does not comprise a proteolytic enzyme. In some embodiments, the contacting step does not result in the substantial breakage of peptide backbone bonds (i.e., amide bonds) in the keratin polypeptide chains.

According to one aspect, the hair sample can range in size from about 2 to about 12 mg per mL of reducing agent solution, e.g., from about 3 to about 10 mg, from about 4 to about 8 mg, from about 7 to about 15 mg, from about 5 to about 10 mg, or from about 8 to about 14 mg per mL of reducing agent solution. The sample can be first washed by known methods to remove analytes or contaminants which may have been deposited on the surface by external contact rather than by actual consumption.

In order to determine the presence and optionally the concentration of one or more analytes, a test sample can be taken from the treated hair sample, either after the contacting step with the reducing solution or after the optional deactivation step. The sample can be removed directly, after the optional deactivation step, or after an optional purification step (e.g., separation, centrifugation, or filtration) to remove residual reduced keratinized sample.

The reducing agent for inclusion in the non-proteolytic reducing solution can be any reducing agent capable of reducing disulfide bonds in keratinized structures, e.g., hair. Typical examples include DTT (2,3 dihydroxybutane-1,4-dithiol) or its isomer DTE (2,3 dihydroxybutane-1,4-dithiol), thioglycolate, cysteine, sulfites, bisulfites, sulfides, bisulfides, 2-mercaptoethanol or TCEP (tris(2-carboxyethyl)phosphine), or salt forms of any of the foregoing.

Typically, the concentration of the non-proteolytic reducing agent in aqueous solution during the contacting step is about 1 to about 20 g/L, e.g., about 1 to about 15, about 2 to about 14, about 5 to about 15, about 10 to about 18, about 3 to about 12, about 4 to about 8, g/L. As one having ordinary skill in the art would recognize, the amount of reducing agent can vary based on the length of the reaction time and the detection methodology to be used.

In some embodiments, the methods may be conducted at or near room temperature and near neutral pH. For example, the method may be performed at a temperature of between about 20° C. and 60° C. (e.g., about 20, 25, 28, 30, 32, 34, 36, 38, 40, 42, 44, 46, 48, 50, 52, 54, 56, or 60° C.) and at a pH between about pH 5 and about 10.5. In some embodiments, the pH of the method is between about 8.8 and 9.7 (e.g., 8.9, 9.0, 9.1, 9.2, 9.3, 9.4, 9.45, 9.5, 9.55, 9.6, 9.65) and the method occurs at a temperature of about 37° C. In other embodiments, e.g., where an analyte of interest or metabolite or degradation product thereof is sensitive to basic pHs, a lower pH can be used, e.g., between about 5 to about 8.7 (e.g., about 5.2, 5.4, 5.6, 5.8, 6.0, 6.2, 6.4, 6.6, 7.0, 7.2, 7.4, 7.6, 7.8, 8.0, 8.2, 8.4, 8.6, or 8.7). Appropriate reaction conditions, including reaction temperature, time, and pH, can be readily determined by those having ordinary skill in the art.

DTT and DTE are particularly useful as reducing agents. It has been found that the use of DTT or DTE in the described processes results in release of the entrapped analytes within a relatively short period of time (depending on the amount and type of keratinized sample), e.g., in about 0.5 to about four hours, or about 1 to about 3 hours, or about 1.5 to about 2.5 hours. In certain embodiments, treatment for about 2 hours is sufficient, e.g., for about 5-15 mg of keratinized sample such as hair.

Once the hair sample has been treated with a solution of a non-proteolytic reducing agent for a time sufficient to release entrapped analytes, e.g., in about 0.5 to about four hours, or about 1 to about 3 hours, or about 1.5 to about 2.5 hours, or about 2 hours, the condition of the hair sample for analyte analysis is assessed.

In one aspect, the condition for analyte analysis after non-proteolytic digestion is assessed visually. Hair samples that exhibit disintegration after non-proteolytic reduction as compared to the control sample (e.g., healthy hair) can be identified as damaged for analyte analysis. Hair samples that appear similar to the control sample (e.g., dissolution at 105-120 minutes) can be identified as intact for analyte analysis. Hair samples identified as extremely damaged may not be suitable for use in subsequent analyte detection methods. In some embodiments, methods disclosed herein include requesting an additional hair sample from an individual when their hair sample has been identified as invalid for hair analyte analysis.

Alternatively, the hair samples identified as damaged may be labeled or flagged as damaged and still analyzed in downstream analyte testing procedures. The labeling alerts the technician performing the downstream analyte testing procedures of the condition and that the results should be monitored and interpreted accordingly. Subsequent washing procedures applied to analyte-positive samples will then be selected based on the hair condition.

In practice, hair samples may be treated with a solution of a non-proteolytic reducing agent (e.g., DTT) under conditions that allow for digestion of the disulfide bonds, and therefore release of analytes from the hair sample, in about 2 hours. After 2 hours, the hair samples are observed for extent of visible degradation of the hair for analyte analysis. In one embodiment, hair samples that appear softened and disintegrated at this 2-hour time-point are identified as damaged for analyte analysis. Such samples may be reported as invalid for analysis. In another embodiment, samples identified as damaged or porous can be labeled damaged, and then used in subsequent analyte detection methods.

In more detail, hair samples that have been treated with a solution of proteolytic reducing agent can be rated on a scale of 1 to 8, 8 being intact hair or "strong" hair (control tubes). An estimate of the state of the weak or porous hair appearance may be 1-2 (completely disintegrated hair), 3-6 (at least partially disintegrated hair with some intact hair), and 7-8 (minimal or no disintegration). Samples having a rating of 1-2 can be identified as porous and damaged for analyte analysis. These samples may be reported as invalid for analysis. Samples having a rating of 4-6 can be identified as damaged or porous, and then used in subsequent analyte detection methods. Such samples can be labeled or flagged as damaged or porous, alerting the technician conducting subsequent analyte detection methods.

Once the analyte(s) have been released into the solution mixture, residual active reducing agent can be optionally deactivated by methods known to those having ordinary skill in the art, including simply waiting a sufficient period of time for deactivation to naturally occur. Typically this time period is from about 2 to about 14 hours after initial contact of the reducing agent with the hair sample, depending on the concentration and amount of reducing agent utilized, the pH, temperature, size of sample, etc. As with the contacting step, the deactivation step is performed in the absence of a proteolytic enzyme (e.g., in a solution consisting essentially of the deactivation agent, or in a solution that does not comprise a proteolytic enzyme).

Alternatively, as known to those having ordinary skill in the art, residual reducing agent can be deactivated with the addition of certain metal ions, typically in the form of metal salts, to the reducing solution. The addition of low amounts, e.g., from about 0.1 to about 1.0 g/L in the final sample solution, of such metal salts to the reducing solution after contacting it with the sample can significantly accelerate the time in which the reduced sample can be subjected to the analyte detection method, since it is not necessary to wait for the reducing agent to deactivate on its own. Most effective are certain metal salts which do not precipitate out of the solution after chemically linking with, and deactivating the reducing agent, such as DTT or DTE. It can be useful to avoid precipitation in the reducing solution because such precipitation could result in a loss of analyte by adsorption to the precipitate or entrapment therein, or could cause interference by particulate obstruction of optical reading methods.

In addition to $Cu^{++}$ salts (e.g., copper sulfate) as described in U.S. Pat. Nos. 5,466,579 and 5,324,642, salts of $Zn^{++}$ (e.g., zinc sulfate and zinc nitrate); $Mn^{++}$ (e.g., manganese sulfate); $Fe^{+++}$ (e.g., ferric sulfate and ferric chloride); and $Fe^{++}$ (e.g., ferrous sulfate) are effective. Also effective are salts of $Pb^{++}$ (e.g., lead acetate and lead nitrate); $Cd^{++}$ (e.g., cadmium chloride); $Hg^{++}$ (e.g., mercuric chloride); $Ag^{++}$ (e.g., silver nitrate); and $Co^{++}$ (e.g., cobalt chloride). See, e.g., U.S. Pat. Nos. 6,022,693 and 6,350,582.

In certain embodiments, a salt of arsenite, such as sodium arsenite ($NaAsO2$), may be utilized to remove residual reducing agent (e.g., DTT or DTE) by formation of a precipitable compound. Typically, 100 microliters of a 100 mg/mL solution of sodium arsenite is added to 1 mL of hair digest solution (final concentration of about 10 g/L) to effectuate the deactivation of the reducing agent. However, arsenite is not preferred because a precipitate can develop, thereby potentially adsorbing or entrapping analyte.

Typically, from about 0.1 to about 1 mg (e.g., about 0.1, 0.2, 0.3, 0.4, 0.5, 0.6, 0.7, 0.8, 0.9, or 1 mg) of a metal salt in solution can be added to about 0.8 to about 1.6 mL (e.g., about 0.8, 0.9, 1.0, 1.1, 1.2, 1.3, 1.4, 1.5 or 1.6 mL) of reducing solution at a time period from about 1 to about 5 (e.g., about 1, 1.5, 2, 2.5, 3, 3.5, 4, 4.5 or 5) hours after contacting the sample with the reducing solution. Typically, the deactivation is rapidly complete, e.g., in less than about 30 minutes, such as in less than about 20 mins., less than about 10 mins., less than about 5 mins., or less than about 2 mins.

Additional information on the methods described herein, including deactivation methods, can be found in U.S. Pat. No. 8,084,215, which is hereby incorporated by reference in its entirety.

In another aspect, the hair sample is subjected to simultaneous proteolytic and non-proteolytic (reduction) methods to release entrapped analytes. In one embodiment, the simultaneous treatment includes contacting the hair sample with one or more proteolytic enzymes, such as papain, chymopapain, and proteinase K, and a reducing agent, such as DTT or DTE. Thus, the treatment method comprises contacting the hair sample with a reducing agent solution, so as to reduce inter- and intra-molecular disulfide bonds in the keratin macrostructure, thereby releasing entrapped analyte, and an enzyme suitable for the dissolution of the hair sample.

Typically, the treatment method comprises an enzymatic digestion in combination with reducing agent step, an optional deactivation step, and an optional purification (e.g., separation, filtration, or centrifugation) step. In the proteolytic step, the sample is contacted with a solution of an enzyme suitable for the dissolution of a keratinized structure, e.g., a proteolytic enzyme, and a reducing agent, such as Dithiothreitol (DTT), thereby releasing entrapped analyte. For methods comprising contacting the hair sample with one or more proteolytic enzymes, the enzyme is selected from the group consisting of peptidase, endopeptidase, and protease, and preferably is papain, chymopapain, or proteinase K.

A number of other proteases have been found to be effective in the method according to the invention at low pH values (e.g., pH 7-9), namely, protease Type IV (bacterial, from *Streptomyces caespitosus*), Type VIII (from *Bacillus subtilis*), Type XI (proteinase K, fungal, from *Tritirachium album*), Type XIV (pronase, from *Streptomyces griseus*), Type XVI (from *Bacillus subtilis*), Type XVIII (Newlase, from *Rhizopus* species), Type XIX (from *Aspergillus sojae*), Type XXI (from *Streptomyces griseus*), Type XXIV (bacterial), Type XXVII (Nagarase), Type III (Prolase) and Type XXIII (from *Aspergillus oryzae*) (all available from Sigma Chemical Co., St. Louis, Mo.).

Once the protein of the hair sample (e.g., the keratinized structure) has been completely or at least substantially dissolved, thereby releasing the analyte into the solution mixture, it has been found to be necessary to deactivate the enzyme and the enzyme/substrate activator(s) in order to subject the analyte to biological analytical probes such as antibodies, since the enzyme and enzyme/substrate activator(s), as noted above, can interfere with the structural integrity of protein substances involved in the analytical method.

According to one aspect, the hair sample can range in size from about 4 to about 16 mg per mL of reducing agent solution, e.g., from about 5 to about 12 mg, from about 6 to about 10 mg, from about 7 to about 15 mg, from about 5 to about 10 mg, or from about 8 to about 14 mg per mL of reducing agent solution. In a one aspect, the hair sample is kept constant at about 5 mg/ml so as to prevent variable matrix effects in subsequently utilized protein-based analytical methods.

In some embodiments, the enzymatic digestion of the hair sample may be conducted at low temperature and near neutral pH. For example, the method may be performed at a temperature of between about 20° C. and 40° C. (e.g., about 20, 25, 28, 30, 32, 34, 36, 38, 40, 42, 44, 46, 48, 50, 52, 54, 56, or 60° C.) and at a pH between about pH 5 and about 10.5. In some embodiments, the pH of the method is between about 8.8 and 10.5 (e.g., 8.9, 9.0, 9.1, 9.2, 9.3, 9.4, 9.45, 9.5, 9.55, 9.6, 9.7, 9.8, 9.9, 10.0, 10.1, 10.2, 10.3, 10.4 or 10.45) and the method occurs at a temperature of about 37° C. Appropriate reaction conditions, including reaction temperature, time, and pH, can be readily determined by those having ordinary skill in the art.

Additional information on the methods described herein, including the optional deactivation methods can be found in U.S. Pat. No. 6,949,344, incorporated by reference. In the proteolytic methods described above, hair samples are generally completely dissolved in about 2 hours. Damaged (e.g., porous) hair samples dissolve more quickly than healthy hair samples. To monitor the rate of dissolution, hair samples undergoing treatment using a proteolytic digestion are observed by a technician at 15 minute intervals. The technician observes and records during the process the extent of hair dissolution or disappearance.

In one embodiment, the appearance of the hair can be rated on a scoring table. For example, a sample that does not significantly dissolve until 105-120 minutes and has no dye color is scored a 8 value, for maximal integrity. These samples are suitable for analyte analysis. Scores for samples with shorter digestion times are as follows: more than 70% digestion at 15 min=1; @ 30 min=2; @ 45 min=3; @ 60 min=4; @ 75 min=5; @ 90 min=6. If a sample shows no dissolution in 120 minutes, this indicates that the hair has been relaxed using an alkaline treatment method, such as a potassium hydroxide (KOH) treatment. Samples having more than 70% dissolution at 15, 30, 45, 60 or 75 minutes can be labeled as damaged or porous. Such samples may be reported as invalid/unsuitable for analysis, or if less damaged, subjected to analytical methods appropriate for porous hair.

Figure 5:
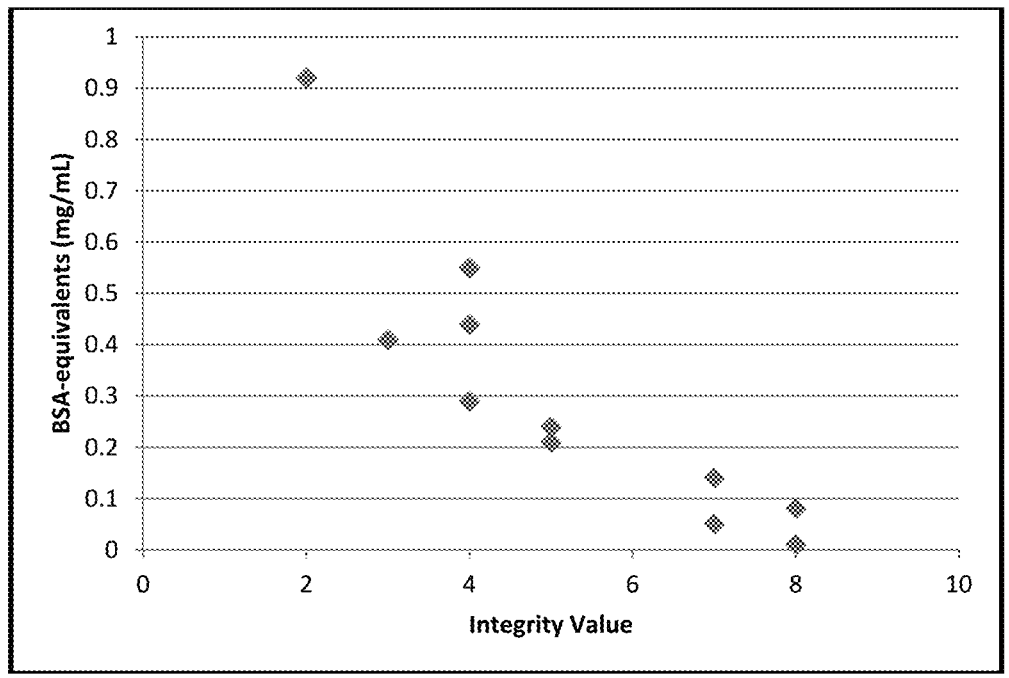
FIG. 5 is graph showing the correlation of protein concentration in the supernatant of a test hair sample following protein denaturation of a test sample after proteolytic digestion (30 minute digestion).

In one aspect, the methods disclosed herein further comprise quantifying the amount of dissolved hair protein for hair samples subjected to the proteolytic and/or non-proteolytic digestion methods described herein. Amongst several methods, dissolved protein is readily determined by the colorimetric method of Lowry et al. (1951), with reference to a standard curve of bovine serum albumin. The colored complex is a result of a complex between the alkaline copper-phenol reagent used and tyrosine and tryptophan residues of the protein, and can be detect by spectrophotometer at 705 nm. Protein concentration is also readily determined by the colorimetric method of Bradford. (distributed commercially by BIO RAD as the BIO RAD PROTEIN ASSAY®). Correlation of protein concentration in the supernatant of the proteolytic digestion at 30 minutes digestion is shown in FIG. 5.

Such assay methods are commonly used for assaying protein in solution and known to those having ordinary skill in the art. Suitable protein assay methods can be found in, e.g., Bradford, "A Rapid and Sensitive Method for the Quantitation of Microgram Quantities of Protein Utilizing the Principle of Protein-Dye Binding", Analytical Biochemistry Vol. 72, pp. 248-254 (1976); Han et al., "A simple improved method for protein extraction from human head hairs", J. Cosmet. Sci., Vol. 58, pp. 527-534 (September/October 2007); Inoue et al., "Elution of 8100A3 from hair fiber: New model for hair damage emphasizing the loss of S100A3 from cuticle", J. Cosmet. Sci., Vol. 51, pp. 15-25 (January/February 2000); Jeong et al., "Hair Damage and Wave Efficiency according to the Degree of Alkalinity in Permanent Wave", Applied Microscopy, Vol. 42(3), pp. 136-141 (2012); Inoue et al., "Labile proteins accumulated in damaged hair upon permanent waving and bleaching treatments", J. Cosmet. Sci., Vol. 53, pp. 337-344 (November/December 2002); Zor et al., "Linearization of the Bradford Protein Assay Increases Its Sensitivity: Theoretical and Experimental Studies", Analytical Biochemistry, Vol. 236, pp. 302-308, Article No. 0171 (1996); Tate et al., "Quantification and prevention of hair damage", J. Cosmet. Sci., Vol. 44, pp. 347-371 (November/December 1993); Sinclair et al., "The proteomic profile of hair damage", British Association of Dermatologists Vol. 166 (Suppl. 2), pp. 27-32 (2012); Davis et al., "Utilizing Proteomics to Characterize Hair and Hair Damage at the Molecular Level", P&G beauty & grooming (undated), the disclosures of each of which are incorporated by reference in their entirety.

Once the treatment of the sample is complete (e.g., non-proteolytic treatment of the hair sample or proteolytic treatment of the hair sample), the hair sample solution may be subjected to direct analysis by art recognized analyte detection methods, including receptor assays, protein-based analytical methods such as immunoassay including radioimmunoassay (RIA) or enzyme immunoassay (EIA), and/or instrumental methods such as mass spectroscopy chromatographic techniques, or atomic absorption.

Additional information on the methods described herein, including methods for determining the presence of an analyte in a sample, can be found in U.S. Pat. No. 8,501,494, U.S. Pat. No. 7,629,129, U.S. Pat. No. 7,618,591, U.S. Pat. No. 7,083,925, U.S. Pat. No. 7,060,453, U.S. Pat. No. 6,949,344, U.S. Pat. No. 6,537,825, U.S. Pat. No. 6,022,693, U.S. Pat. No. 5,981,204, U.S. Pat. No. 5,910,419, U.S. Pat. No. 5,324,642, U.S. Pat. No. 4,956,467, EP 2518474, WO 2014/005065, WO 2005/121793, WO 2005/039381, WO 2003/031935, Harrison, R. and Fu, S., J. Forensic Sci., Vol. 2(1): 1-8 (January 2014), Koster et al., Therapeutic Drug Monitoring, Vol. 36(2): 234-243 (April 2014), Vincenti et al., Bioanalysis, Vol. 5(15): 1919-1938 (August 2013), Lopez-Guarnido et al., J. Applied Toxicology, Vol. 33(8): 838-844 (August 2013), Kronstrand et al., Therapeutic Drug Monitoring, Vol. 35(3): 288-295 (June 2013), Cooper et al., Forensic Sci. Int., Vol. 218(1-3): 20-24 (May 2012), Albermann et al., Anal Bioanal Chem, Vol. 400: 175-181 (2011), Musshoff, F. and Madea, B., Anal Bioanal Chem, Vol. 388: 1475-1494 (2007), Gratacos-Cubarsi et al., Journal of Chromatography B., Vol. 834: 14-25 (2006), Nielen et al., J. Chrom. B., Vol. 830: 126-134 (2006), Pascal et al., Therapeutic Drug Monitoring, Vol. 26(2): 211-214 (April 2004), Chan et al., Clinical Biochemistry, Vol. 37(6): 429-138 (June 2004), Dolan et al. Drug and Alcohol Review, Vol. 23(2): 213-217 (2004), Villain et al., Forensic Sci. Int., Vol. 145(2-3): 117-121 (October 2004), Kintz, Legal Medicine, Vol. 5(Supplement): S29-S33 (March 2003), Baptista et al., Forensic Sci. Int., Vol. 128: 68-78 (August 2002), Lewis et al., Forensic Sci. Int., Vol. 84(1-3): 123-128 (January 1997), Yegles et al., Forensic Sci. Int., Vol. 84(1-3): 211-218 (January 1997), Polettini et al., Forensic Sci. Int., Vol. 84(1-3): 259-269 (January 1997), Kintz et al., J. Forensic Sci., Vol. 40(4): 619-22 (July 1995), Kintz et al., J. Chromatography B: Biomedical Sciences and Applications, Vol. 670(1): 162-166 (August 1995), Ahrens et al., J. Anal. Chem., Vol. 344: 559-560 (1992), and Baumgartner et al., J. Nuclear Med., Vol. 20: 748-752 (1979), which is hereby incorporated by reference in its entirety.

In particular embodiments, instrumental methods (e.g., a mass spectrometry technique or a chromatographic technique) may be used to confirm positive results obtained in immunoassay methods. Because these methods are not protein-based, the step of deactivation of reducing agent is not necessary. The speed and gentleness of the treatment method and the ability to quantitate efficiency through the inclusion of a "spike," i.e., the inclusion of a known amount of deuterated analyte, makes the presently disclosed treatment method also the method of choice for instrumental analysis methods such as gas chromatography, liquid chromatography and mass spectrometry. The method can be used to detect the use and prior use of any analyte of interest described previously, including drugs of abuse such as cocaine, morphine/heroin and other opioids, cannabinoids, marijuana, phencyclidine or "PCP," methaqualone, and amphetamines. Moreover, the method can be effective in determining prior usage of prescription drugs such as digoxin, methadone and benzodiazepines. It is contemplated that any analyte, particularly any organic analyte, present in the bloodstream of an individual which is transferred to the hair during its synthesis can be extracted and analyzed in accordance with the methods described herein.

In some aspects, a detergent can be used to aid in the release of one or more analytes of interest from the hair sample. Certain biological detergent compounds useful for solubilizing biological membrane components aid in the release of the analytes at a relatively low pH while not interfering with reduction or subsequent analyte detection. These biological detergents can aid the in the treatment of a keratinized sample at a pH in the range of about 5 to about 10.5. Suitable detergents include bile acid detergents, such as glycocholic acid, cholic acid, taurocholic acid, deoxycholic acid, glycodeoxycholic acid, taurodeoxycholic acid and salts thereof, including sodium salts. Other detergents for use in the methods are sulfo-betaines, such as the Zwittergents® and betaines, such as Empigen BB (N-dodecyl-N,N-dimethylglycine) (all available from Calbiochem Corp., La Jolla, Calif.). Other detergents include alkylglucosides, including hexyl-beta-D-glucopyranoside, heptyl-beta-D-glucopyranoside, octyl-beta-Dglucopyranoside, nonyl-beta-D-glucopyranoside, decyl-beta-D-glucopyranoside, dodecyl-beta-D-maltoside and octyl-beta-D-thioglucopyranoside (OSGP). Mixtures of alkylglucosides, such as the product ELUGENT® (Calbiochem), are also effective. Particularly preferred are the bile acids cholic acid and glycocholic acid, which aid in the digestion of hair at a pH in the range of about 6.3 to about 8. The deoxycholates such as deoxycholic acid and glycodeoxycholic acid are effective in aiding in the digestion of hair at a pH above about 7.

The detergents can be used in the industry standard five-drug screen for the most common drugs of abuse in the United States, i.e., marijuana, cocaine, phencyclidine, methamphetamine and opioids, measured using the methods described herein. Thus, they do not impact any of the analytes or antibodies involved in the five-drug screen, and do not result in false negatives or positives. The particular detergents most effective for use in the five-drug screen are cholate, deoxycholate, cholic acid, deoxycholic acid, octyl-beta-D-glucopyranoside and octyl-beta-D-thioglucopyranoside. The bile acid detergents, alkylglucosides, sulfobetaines and betaines are preferred when a screen is performed that includes cocaine, opioids, phencyclidine, amphetamines and sympathomimetic amines. In a screen solely for cocaine, the preferred detergents are cholic acid, Zwittergents®, alkylglucoides, and N-dodecyl-N,N dimethylglycine.

In practice, the biological detergent is mixed with the aqueous reducing solution prior to contact of the solution with the keratinized sample at a temperature range of about 30 to about 40° C. Typically, about 1-2 mg of biological detergent is added to about 1 ml of reducing solution.

Additional information on the methods described herein, including the use of biological detergents, ion exchange resins (e.g., to remove interfering substances), and varying pH ranges for digestion, can be found in U.S. Pat. Nos. 6,022,693 and 6,350,582, incorporated herein by reference in its entirety.

In some embodiments, the methods disclosed herein further comprise indicating the hair sample as unsuitable for determining if the analyte is present in the test solution when the hair sample has been identified as damaged. For hair samples identified as damaged or identified as unsuitable for determining if the analyte is present, the methods can further comprise requesting a new sample from the subject. The new sample can be a new keratinized sample (e.g.,) new hair sample or other sample suitable for use for testing for the presence and/or amount of one or more analytes of interest.

Any type of sample can be tested for the presence and/or amount of one or more analytes of interest. In certain cases, a sample contains or is suspected to contain one or more analytes of interest, such as one or more drugs of abuse or toxic chemicals. A sample can be a bodily sample or a non-bodily sample. A bodily sample (e.g., a hair sample) can be a specimen obtained from an individual (e.g., a human, mouse, rat, pig, horse, monkey, rabbit, cow, sheep, or goat). A bodily sample can be a tissue sample, such as a tissue sample of the brain, heart, lungs, kidneys, liver, muscle, bone, stomach, intestines, or skin. A bodily sample can be obtained by biopsy or from tissue culture. A bodily sample can include a biological fluid such as urine, blood, plasma, serum, saliva, semen, sputum, cerebral spinal fluid, mucus, sweat, milk, vitreous fluid and the like. A bodily sample can be a keratinized structure, such as hair, a fingernail, or a toenail. A non-bodily sample can be, for example, a soil or water sample, a plant sample, an inorganic material sample, or a sample from a research or manufacturing process.

A sample can be used as is, or can be treated to result in a final sample for detection of the one or more analytes. For example, a sample can be liquefied, concentrated, dried, diluted, lyophilized, extracted, fractionated, subjected to chromatography, purified, acidified, reduced, degraded, subjected to enzymatic treatment, or otherwise treated in ways known to those having ordinary skill in the art in order to release an analyte of interest. If desired, a sample can be a combination (pool) of samples, e.g., from an individual or from a manufacturing process.

A sample can be in a variety of physical states, e.g., liquid, solid, emulsion, or gel. Samples can be treated with customary care to preserve analyte integrity. Treatment can include the use of appropriate buffers and/or inhibitors, such as inhibitors of certain biological enzymes. One having ordinary skill in the art will be able to determine the appropriate conditions given the analytes of interest and the nature of the sample.

In some embodiments, a sample is derived from a bodily sample.

In some embodiments, a sample is derived from a keratinized structure. In some embodiments, the keratinized structure is hair.

In one aspect, the disclosure provides methods for determining if an analyte is present in a hair sample after the hair sample has been identified as damaged or as having increased porosity. As shown in the examples, it is possible to excessively wash damaged or porous hair using an aqueous wash solution, resulting a false negative result. The fact that some drug may wash out in a damaged or porous hair sample does not necessarily disqualify the sample from further analyte testing. Rather, the hair sample can be washed with a non-swelling solvent (e.g., ethanol) prior to the assessing and/or determining steps.

In some embodiments, the methods disclosed herein further comprise subjecting a hair identified as damaged or as having increased porosity to an ethanol washing procedure as described herein, and determining if the analyte is present in the hair sample. In one embodiment, the ethanol was procedure comprises soaking the hair sample two, three, four, five, or six times in 90% ethanol. For example, the hair sample is soaked in 90% three times for 30 minutes and then soaked in 90% ethanol for two 60 minute washes. The last wash sample may then be analyzed to determine the presence of an analyte.

Additionally, the degree to which an analyte if retain within, or elutes from a damaged, porous hair sample depends, in part, on the analyte. Specifically, some drug analytes are retained within a damaged, porous hair sample more readily than other drug analytes. For instance, as shown in the examples, methamphetamine and metabolites thereof are retained within porous hair samples more readily than cocaine. Thus, depending on the analyte of interest, it is possible, even recommended to complete the determining step for hair samples identified as damaged or as having increased porosity.

In some embodiments, the methods disclosed herein comprise determining if an analyte is present in a hair sample which has been identified as damaged or as having increased porosity for analytes which are likely to be retained with damaged, porous hair. For analytes which do not readily elute from damaged, porous hair., the methods may be further modified to include a step of subjecting a hair identified as damaged or as having increased porosity to an ethanol washing procedure as described herein, and determining if the analyte is present in the hair sample.

The benefits to be obtained from the presently disclosed methods are many, including a prompt, accurate, and inexpensive determination of prior exposure to a particular analyte, after assessment of whether the sample is in suitable condition for analysis. The method can provide a record of consumption, or non-consumption, over very long periods of time. Moreover, hair collection is less intrusive and less physically repulsive than blood or urine collection, and samples cannot be altered or substituted, nor can detection be evaded by short term abstention or "flushing" (excessive fluid intake) prior to a scheduled testing, e.g., pre-employment test or annual physical examination. Samples may be stored indefinitely without refrigeration. Finally, the methods facilitate both screening and confirmatory assays for detecting an analyte of interest.

The following examples are meant to be illustrative and do not limit the claims.

EXAMPLES

Three new methods (Examples 1-3) to characterize the condition of hair samples, the methods for which are presented below, include (1) observation of dissolution of hair in a non-proteolytic system containing a reducing agent; (2) observation of the rate of dissolution in a solution containing reducing agent and a proteinase; (3) measurement of protein leakage from hair samples when exposed for 2 hours to a non-proteolytic system containing reducing agent; and (4) measurement of protein leakage from hair samples when exposed for 2 hours to a proteolytic system containing reducing agent.

Example 1

Hair Integrity Test of Non-Proteolytic Hair Digests

A solution of dithiothreitol (0.3% DTT, adjusted to pH 9.5 with KOH) was added to hair samples (5 mg hair per mL) and incubated for 2 hours. The samples were placed in a 37° C. water bath with shaking at 110 oscillations per minute (opm) for 2 hours. After 2 hours the samples were observed for the extent of visible hair degradation. Samples that have not been subjected to cosmetic treatments or that have been subjected to normal cosmetic procedures appear essentially intact. Damage hair samples, however, appear softened and have disintegrated at this point (FIG. 1). As shown in FIG. 1, the first two samples are nearly destroyed at the end of 2 hours, the third sample is partially destroyed, and the two control samples (untreated virgin hair) remain visually unchanged still have intact-appearing hair strands.

Hair samples that are partially or fully dissolved are identified as damaged. Alternatively, the samples can be further evaluated using the proteolytic method and rated on a scale of 1 to 8, with 8 being intact/control hair. An estimate of the state of damaged hair appearance may be 1-2 (tubes 1 and 2), 4-5 (tube 3) and 7-8 (tubes 4 and 5).

Example 2

Hair Integrity Test of Proteolytic Hair Digests

A solution of dithiothreitol and proteinase K (Sigma P6556), (0.6% DTT, 0.25 units/ml proteinase K, adjusted to pH 9.5 with KOH) was added to hair samples (5 mg hair per mL) and incubated for 2 hours. Nonporous intact hair in this solution, at 37° C. with shaking, requires about 2 hours to dissolve completely, while damaged hair dissolves more quickly—the more damaged the hair the more quickly it dissolves. The state of the hair samples is noted at 15-minute intervals, and integrity values are assigned depending on the time-point at which the sample dissolves. Integrity values of 1-8 (1=15 min and 8=120 min) were assigned to correspond to the 8 time-points of dissolution.

As shown in FIG. 2, a series of photographs were taken at 15-minute intervals to visualize the rate of dissolution. At these 15 minute intervals the condition of the hair samples in the tube is assessed by visual inspection and recorded. As part of the assessment, the technician observed and recorded the hair solubilization, or simply its disappearance. A hair sample that does not significantly dissolve until 105-120 minutes is recorded as having maximal integrity (integrity value of 8). Samples having more than 70% dissolution at 15, 30, 45, 60 and 90 minutes are rated as porous and therefore damaged. Referring to FIGS. 2A-F, samples 2, 3, 5 and 7 have more than 70% dissolution at 75 minutes. Thus samples 2, 3, 5 and 7 are rated as porous and damaged.

A sample that does not reach 70% dissolution by 90 minutes is not rated as overly porous. For example, samples 1, 4, 6 and 8 have less than 70% dissolution by 90 minutes, and are rated as healthy or intact hair samples.

Example 3

Measurement of Protein Leakage from Damaged Hair During Non-Proteolytic Digestion For this example, the inventors determined hair porosity by performing a protein analysis of nonenzymatically (nonproteolytic) digested samples at the two-hour endpoint to quantify the amount of solubilized hair proteins released from the hair. The proteins measured in the protein assay may be those solubilized or made "labile" by the cosmetic treatments themselves, as well as proteins released through the action of the reducing agent (e.g. DTT or DTE) penetrating more readily the porous hair samples.

Using the Bradford protein assay, a standard curve using bovine serum albumin in concentrations of 0.25, 0.5, 1.0, 1.5 and 2.0 mg/mL is determined as a reference. In a 96-well microplate, 2.5 uL of standards and samples were combined in the wells along with 300 uL of Coomassie Blue reagent (Biorad). The samples were mixed and read after 5-10 minutes at 595 mu in a microplate reader. At this sample volume, there was no interference of dithiothreitol in the assay.

Example 4

Materials and Methods

Methylene Blue Staining:

Hair can be identified as porous or nonporous by a previously published method of staining with methylene blue.[19] Use of methylene blue to identify cosmetically and mechanically damaged hair has also been presented by Roe[20] and Kuzuhara[21]. The procedure, although somewhat laborious and impractical in a high through-put laboratory, provides evidence of porosity in cases of permed, bleached, dyed or mechanically damaged hair, and has been routinely used in this laboratory for this purpose. Four new methods to characterize the condition of hair samples, the methods for which are presented below, include (1) observation of dissolution of hair in a non-proteolytic system containing a reducing agent (e.g., DTT or DTE)[22,23]; (2) observation of the rate of dissolution in a solution containing reducing agent (e.g., DTT or DTE) and a proteinase suitable for digestion of keratin (e.g., proteinase K)[24]; (3) measurement of protein leakage from hair samples when exposed for 2 hours to a non-proteolytic system containing reducing agent (e.g., DTT or DTE); and (4) measurement of protein leakage from hair samples when exposed to a proteolytic system containing reducing agent and proteolytic enzyme.

Nonproteolytic Digestion System to Identify Damaged Samples:

The nonproteolytic digestion method consists of 5 mg hair per mL of 0.3% dithiothreitol (Sigma D0632) adjusted to pH 9.5 with KOH. The samples are placed in a 37° C. water bath with shaking at 110 oscillations per minute (opm) for 2 hours. After 2 hours the samples are observed and those showing dissolution are noted. Only exceptionally damaged samples show such dissolution in this system. Samples that have not been subjected to cosmetic treatments or that have been subjected to normal cosmetic procedures appear essentially intact. Only about 0.5% of samples demonstrate dissolution at 2 hours in the nonproteolytic digestion. These samples are tested again by the proteolytic method, described below.

Proteolytic (Enzymatic) Digestion System to Identify Damaged Samples:

The proteolytic digestion method consists of 5 mg hair per mL of a solution of 0.6% dithiothreitol at pH 9.5 containing 0.25 unit/mL of Proteinase K (Sigma P6556). Nonporous intact hair in this solution, at 37° C. with shaking, requires about 2 hours to dissolve completely, while damaged hair dissolves more quickly—the more damaged the hair the more quickly it dissolves. The state of the hair samples is noted at 15-minute intervals, and integrity values are assigned depending on the time-point at which the sample dissolves. Integrity values of 1-8 (1=15 min and 8=120 min) were assigned to correspond to the 8 time-points of dissolution. Correlation of these values to known severities of cosmetic treatments will be shown in Results.

The effects of cosmetic treatments in these systems were tested with laboratory-treated hair samples. Each treatment was applied to three samples. For perming hair, the product used was "Feels So Lively," Alkaline Perm for Resistant Hair, Zotos International, Inc. Hair was exposed to the perming solution for the recommended 12 minutes, rinsed under running tap water, neutralized, rinsed again, and then dried.

To relax hair, the product applied was "Soft and Beautiful No-Lye Relaxer System," Unilever Corporation. Relaxer components were combined according to kit instruction, applied with an applicator stick, massaged into the hair, and allowed on the hair for 15 minutes. The sample was rinsed and neutralizing shampoo applied repeatedly until no pink indicator color was visible. The samples were rinsed under running tap water and then allowed to dry.

Bleaching was performed with "L'Oréal Super Blonde Crème Lightening Kit," L'Oréal Group. Solutions were prepared according to kit instructions, and applied with massage into the hair. The bleach was allowed on the hair for the recommended 25 minutes, and then rinsed under running tap water and dried.

In addition, a hair sample with known professional cosmetic treatments and untreated control samples were taken from children's hair cuts with no hair treatments were tested.

Measurement of Protein Leakage from Damaged Hair During Nonproteolytic Digestion:

The inventors also investigated another means of determining hair porosity by performing a protein analysis of the nonenzymatically (nonproteolytic) digested samples at the 2-hour endpoint to quantify the amount of solubilized hair proteins released from the hair. The proteins measured in the protein assay may be those solubilized or made "labile" by the cosmetic treatments themselves[26], as well as proteins released through the action of dithiothreitol penetrating more readily the porous hair samples.

Using the Bradford protein assay,[26] a standard curve using bovine serum albumin in concentrations of 0.25, 0.5, 1.0, 1.5 and 2.0 mg/mL is determined as a reference. In a 96-well microplate, 2.5 uL of standards and samples were combined in the wells along with 300 uL of Coomassie Blue reagent (Biorad). The samples were mixed and read after 5-10 minutes at 595 mu in a microplate reader. At this sample volume, there was no interference of dithiothreitol in the assay.

Wash Methods:

The aqueous wash procedure and application of the wash criterion have been extensively presented previously.[15-18] Briefly the method consists of 10-12 mg hair in 2 mL of an initial non-swelling 15-min dry isopropanol wash in a 37° C. 110-opm shaking water bath, followed by three 30-min washes and two 60-min washes in 0.01 M phosphate buffer (pH 6) containing 0.1% bovine serum albumin (BSA), also in a 37° C. 110-opm shaking water bath. The initial non-swelling isopropanol wash serves to remove drug that may be only on the surface of the hair, prior to adding the hair-swelling solution that could allow such surface drug to penetrate the hair. The last wash is analyzed for the drug of interest. The wash criterion for cocaine is as follows: if the amount of drug in the last wash multiplied by 5 and then subtracted from the amount of drug in the hair results in a value below the cutoff, this is an indication that the sample may be contaminated or porous. This calculation is essentially a mathematical extrapolation of the washing by another 5 hours, as an indication of whether or not all the drug would be washed out; this is, of course an overestimate of drug removal since the wash kinetic curve is never that linear, and if anything errs on the side of safety in protecting the subject from being reported as positive from environmental contamination. For amphetamines, the wash criterion has been determined empirically to be optimal when the last wash is multiplied by 3.5 and the result subtracted from the amount of drug in the hair.[15,17]

The ethanolic wash method presented herein, first noted in 1992 as an alternative wash for porous samples,[27] consists of three 30-min and two 60-min washes in 90% ethanol, also performed in a 37° C. 110-opm shaking water bath. The last wash is analyzed for the drug of interest by first acidifying the sample (to prevent volatilization of the amphetamines) and then evaporating the ethanol, followed by reconstituting the sample in 0.01 M phosphate buffer (pH 6) containing 0.1% BSA.

Wash samples are analyzed either by LC/MS/MS, by the same procedures as described below for extracts of hair samples, or by quantitative enzyme immunoassays developed in this laboratory for analysis of hair washes.

In Vitro Contamination of Hair Samples with Cocaine or Methamphetamine:

To test the need for extended exposure to aqueous or swelling solvents for effective washing, samples from ponytails were soaked in 10 ug cocaine/mL water for 1 hour, rinsed and dried overnight. In addition to washing by the extended washing methods described above, short exposures to two different nonswelling solvents, dichloromethane and methanol, were also tested. In each case, the 11-12 mg of the hair samples were washed twice with 2 mL of the solvents for 2 minutes each with gentle vortexing, and the washes and washed hair analyzed for cocaine and amphetamines. Total drug on the hair was calculated by addition of the drug in the washes and in the hair.

Confirmation Procedures—Cocaine:

The washed hair was enzymatically digested at pH 5.5 as previously described.[14,17,18] Digest supernatants were extracted using Isolute SPE columns. Eluted samples were dried and 25 uL of N,N-dimethylformamide dipropyl acetal was added, with heating at 120° C. for 5 minutes, to effect the derivatization of benzoylecgonine, to ensure separation of norcocaine from the benzoylecgonine.

LC/MS/MS analysis of cocaine and metabolites was performed on a Perkin Elmer Sciex triple quadrupole API 2000 (Thornhill, On, Canada) MS, operating in the positive chemical ionization mode, linked to two Perkin Elmer Series 200 micropumps and a Perkin Elmer Series 200 autosampler. Mass resolution on Q1 and Q3 were set to unit resolution. Interface heater was ON, Turbo ion spray voltage was 5500V; Turbo gas temperature was 350° C. to 400° C.; in Positive Reaction Mode. The mobile phase was 33% acetonitrile and 0.1% formic acid and 67% water with 0.1% formic acid. Isocratic mode was used. The HPLC column was a Keystone Scientific BETASIL C8, 2 mm×50 mm, 5 µm particle size; a flow rate of 300 µL/minute was used. For LC, the autosampler with two micropumps used a 5 µm sample loop volume, 10 µL injection volume, 500 µL flush volume, and a flush solvent of acetonitrile:water: formic acid (30:70:1). The transitions for cocaine and its internal standard cocaine-d3 were m/z 304.1>182.1 and m/z 301.1>185.1, respectively; for derivatized benzoylecgonine and its d3-internal standard, m/z 332.1>210 and m/z 335.1>213; for cocaethylene and its d3-internal standard, m/z 318.1>196 and 321.1>199; for norcocaine and its d3-internal standard, m/z 290.1>168 and m/z 293.1>171.

Confirmation Procedures—Methamphetamine:

The washed hair was enzymatically digested at pH 6.65 as previously described.[15] Digest supernatants were extracted with a liquid/liquid extraction method. LC/MS/MS analysis of amphetamines was performed on a Perkin Elmer Sciex triple quadrupole API 2000 (Thornhill, On, Canada) MS, operating in the positive chemical ionization mode, linked to two Perkin Elmer Series 200 micropumps and a Perkin Elmer Series 200 autosampler. Mass resolution on Q1 and Q3 were set to unit resolution. Interface heater was ON, Turbo ion spray voltage was 5500V; Turbo gas temperature was 350° C. to 400° C.; in Positive Reaction Mode. The mobile phase was 11% acetonitrile with 0.1% formic acid and 89% water with 0.1% formic acid. Isocratic mode was used. The HPLC column was a Keystone Scientific BETASIL C8, 2 mm×50 mm, 5 µm particle size; a flow rate of 300 µL/minute was used. For LC, the autosampler with two micropumps used a 5 µL sample loop volume, 10 µL injection volume, 500 µL flush volume, and a flush solvent of acetonitrile:water: formic acid (30:70:1).

The target ions for methamphetamine and its internal standard methamphetamine-d11 were m/z 150<91 and m/z 161>96, respectively; for amphetamine and its internal standard amphetamine-D8, m/z 136>91 and m/z 144>96; for MDMA and its internal standard MDMA-D5, m/z 194>135 and m/z 199>136; for MDEA and its internal standard MDEA-D6, m/z 194>163 and m/z 199>166. Specificity studies ruled out interference from ephedrine, fenfluramine, pseudoephedrine, phentermine and phenylpropanolamine.

Results: Hair Integrity Testing

Cosmetic Treatments and Rate of Sample Dissolution in Proteolytic Digestion

As described in Methods, previously untreated hair samples were cosmetically treated with bleach, perm, and relaxer, and then subjected to the timed proteolytic digestion. Also, some hair samples known to have no prior cosmetic treatments and one with known professional cosmetic treatments were tested. As shown in Table 1, the untreated control samples dissolved at the 105-120-minute timing, while treated samples dissolve earlier depending on the severity of the treatments. Normal perm or bleach treatments, following the vendors' instructions, resulted in shorter digestion times than the controls, usually in the range of 60-90 minutes, with assigned Integrity Values of 4-6, as described in Methods. When excessive bleaching was intentionally performed, the samples digested more quickly with each additional treatment, with 3 bleachings dissolving in 30 minutes (Integrity Value of 2). The salon-dyed hair, from a female who has the roots dyed approximately monthly, dissolved in 90 minutes. Permanent dyeing of hair usually involves some mild bleaching along with the dye, and it can be assumed that it is the bleach that causes the hair damage.

TABLE 1

Control and Laboratory Cosmetically Treated Samples in Proteolytic Digestion

| Type of Sample | Time for Hair to Dissolve (minutes) | Integrity Value |
|---|---|---|
| Control: Haircut, male | 120 | 8 |
| Control: Ponytail-1, female | 105 | 7 |
| Control: Ponytail-2, female | 120 | 8 |
| Female -white hair, routinely salon dyed | 90 | 6 |
| Permed #1 | 75 | 5 |
| Permed #2 | 90 | 6 |
| Permed #3 | 75 | 5 |
| Bleached #1 | 60 | 4 |
| Bleached #2 | 60 | 4 |
| Bleached #3 | 60 | 4 |
| Bleach #3 twice (excess) | 45 | 3 |
| Bleach #3 times (extreme) | 30 | 2 |

TABLE 1-continued

Control and Laboratory Cosmetically Treated
Samples in Proteolytic Digestion

| Type of Sample | Time for Hair to Dissolve (minutes) | Integrity Value |
|---|---|---|
| Relaxed #1 | Did not dissolve | Porous* |
| Relaxed #2 | Did not dissolve | Porous* |
| Relaxed #3 | Did not dissolve | Porous* |

*See text for experiment performed with relaxed hair to demonstrate porosity.

Samples with integrity values of 2 or less are excessively damaged samples, as shown with the triple-bleached sample, and may be reported as invalid or unsuitable samples for testing for drug use, since such damage can remove any drug deposited due to ingestion during the treatment itself and in subsequent repeated shampooing, resulting in a false negative report of drug ingestion. Integrity values from 3 to 6 indicate sufficient porosity to influence results of aqueous washing of the hair sample, since the increased porosity will allow drug deposited from ingestion to diffuse out of the hair in an aqueous hair-swelling wash buffer. Integrity values of 7 indicate slight porosity, and 8 indicates an intact sample.

Table 1 also shows a major exception to the rapid enzymatic digestion of cosmetically treated hair—that of hair that has been relaxed or straightened using very highly basic crème applied to the hair with combing to straighten the strands (e.g., SoftSheen Optimum Care No-Lye Relaxer). With this treatment the hair does not dissolve at all at 2 hours of enzymatic digestion (in fact, a relaxed hair does not dissolve in 24 hours). This characteristic of relaxed hair actually provides the test for identifying relaxed hair, since normal hair dissolves by 120 minutes. In order to determine whether hair is rendered porous by the relaxing treatment, we selected three cocaine-positive samples previously shown to be intact, nonporous samples by the fact that the last wash contained very little cocaine, i.e., the drug present in the hair from ingestion did not diffuse into the aqueous wash solution (Table 2). These samples were relaxed as described in Methods, and the relaxed samples subjected to the aqueous wash procedure. It can be seen that more drug diffused into the washes after the samples had been relaxed. High cocaine values in the wash or failed wash criterion normally would indicate that the samples were contaminated or porous, but in this case we had selected samples that were not contaminated, so the failed washes after aqueous washing indicate porosity. Thus, if a sample does not dissolve in the proteolytic digestion, this indicates the hair is relaxed and porous.

Dissolution of Hair in Nonproteolytic Digestion System

Evidence of resistance of most hair samples to digestion in the nonproteolytic system is that over 99% of many thousands of samples have not shown dissolution at the 2-hour point. Examples of samples that do show disintegration at this time point and were also tested with the proteolytic system to confirm the initial result are shown in Table 3. The proteolytic test, which provides a clearer estimation of porosity, is always performed on those samples identified in the nonproteolytic system to confirm the first visual identification of an extremely damaged hair. Samples that dissolve in 30 minutes or less in the proteolytic system (Integrity Values of 1 or 2) are severely damaged, as we showed in our testing of laboratory-treated samples.

TABLE 3

Proteolytic Test of Samples that Dissolved
at 2-hours in Nonproteolytic Digestion

| Sample description | Time for Hair to Dissolve (minutes) | Integrity Value |
|---|---|---|
| Blond, straight | 45 | 3 |
| Black, straight, dyed | 30 | 2 |
| Brown, straight | 45 | 3 |
| Brown, straight | 30 | 2 |
| Blond, straight | 45 | 3 |
| Brown, straight | 30 | 2 |

Measurement of Protein Leakage from Damaged Hair During Nonproteolytic Digestion The correlation of results of the proteolytic digestion method for porosity and the protein assay performed on nonproteolytic digests are shown in FIG. 5. Some of the samples shown in the correlation were treated in the laboratory, using commercial perming or bleaching kits, and others were unknown samples characterized by the porosity testing by digestion rate. Relaxed hair is again an exception in that protein is not released with these samples. Therefore, the integrity test consisting of enzymatic digestion rates appears to be the only method available at this time for identifying relaxed hair. Another shortcoming of this protein assay to measure severity of damage is that very severely damaged samples may leak so much protein that they exceed the range of the assay, causing precipitation and producing an artificially low reading. The artifact can be managed by observing the precipitate in the wells and performing multiple greater dilutions of the samples.

In Vitro Contamination Studies

Extended Washing with 90% Ethanol

TABLE 2

Effect of Relaxing on Hair Porosity: Nancontaminated Cocaine-Positive Hair Samples
Before and After Relaxing Treatment

| | Intact Samples before Relaxing | | | | | | Samples after Relaxing | | | | | |
|---|---|---|---|---|---|---|---|---|---|---|---|---|
| | COC | BE | Last Wash | | Wash | | COC | BE | Last Wash | | Wash | |
| Sample | ng/10 mg hair | | | % BE | Criterion | Interpretation | ng/10 mg hair | | | % BE | Criterion | Interpretation |
| 1 | 160 | 21.9 | 7.7 | 13.7 | 121.5 | Positive | 66 | 7.9 | 16.4 | 12.0 | −16 | Contaminated or Porous |
| 2 | 44.8 | 4.8 | 1.5 | 10.8 | 37.1 | Positive | 47.7 | 4.8 | 8.2 | 10.1 | 6.7 | Positive |
| 3 | 499.9 | 60.7 | 1.4 | 12.1 | 492.9 | Positive | 340.1 | 35.1 | 108.6 | 10.3 | −202.9 | Contaminated or Porous |

In a preliminary test of 90% ethanol washing, hair samples taken from ponytails purchased from a salon were soaked for 70 minutes in a water solution of 10 ug/mL cocaine (COC)

and methamphetamine (METH), a serious challenge to a washing procedure that needs to identify contamination at the 5 ng/10 mg hair level. The samples were removed after soaking, rinsed under running tap water, and allowed to dry overnight. Samples were weighed and then washed with the 90% ethanol procedure, with results shown in Tables 4 (cocaine) and 5 (methamphetamine). The large amount of drugs remaining in the hair after washing reflects the highly concentrated soaking conditions. Application of the wash criterion, however, clearly identified all samples as negative or contaminated, as seen by the negative values after its application.

TABLE 4

90% Ethanol Washing of Samples Soaked in 10 ug/mL Cocaine

| | ng/10 mg hair | | | |
|---|---|---|---|---|
| Sample # | (A) Cocaine in Hair After Washing | (B) Cocaine in Last Wash | Wash Criterion (A) − 5x(B) | Result* |
| 1 | 43.1 | 26.6 | −89.9 | Negative/Contam |
| 2 | 93.9 | 40 | −106.1 | Negative/Contam |
| 3 | 47.8 | 31.2 | −108.2 | Negative/Contam |
| 4 | 36 | 17.3 | −50.5 | Negative/Contam |
| 5 | 77.7 | 18.7 | −15.8 | Negative/Contam |
| 6 | 54.8 | 18.7 | −38.7 | Negative/Contam |
| 7 | 53 | 29 | −92 | Negative/Contam |
| 8 | 42.2 | 25.1 | −83.3 | Negative/Contam |
| 9 | 78 | 34 | −92 | Negative/Contam |

TABLE 5

90% Ethanol Washing of Samples soaked in 10 ug/mL Methamphetamine

| | ng/10 mg hair | | | |
|---|---|---|---|---|
| Sample # | (A) Meth in Hair After Washing | (B) Meth in Last Wash | Wash Criterion (A) − 3.5x(B) | Result* |
| 1 | 77.8 | 53.5 | −109.4 | Negative/Contam |
| 2 | 123.5 | 51.6 | −57.1 | Negative/Contam |
| 3 | 74 | 81.8 | −212.3 | Negative/Contam |
| 4 | 121.3 | 53.3 | −65.2 | Negative/Contam |
| 5 | 50.6 | 24.6 | −35.5 | Negative/Contam |
| 6 | 103.9 | 34.9 | −18.2 | Negative/Contam |
| 7 | 74.3 | 25.8 | −16 | Negative/Contam |
| 8 | 242.9 | 81.8 | −43.4 | Negative/Contam |

Short Washes with Alternate Solvents

The inventors were interested in non-hair-swelling solvents for possible washing of porous hair, and therefore also tried short exposures to two different solvents, dichloromethane and methanol (Table 6). For all but one of the dichloromethane-washed samples, less than 2.5% of the contamination was removed; in one case 8.7% was removed by the washing. In the case of methanol washing, 2.2 to 12.9% of the COC was removed, with one case being above 10%. These results support the need for lengthy washing in at least partially hair-swelling solvents along with an indicator or criterion to estimate the effectiveness of the decontamination process.

TABLE 6

Dicchloromethane and Methanol Washing of Cocaine-Soaked Hair Samples

| | Dichloromethane Washing | | | | Methanol Washing | | | |
|---|---|---|---|---|---|---|---|---|
| Sample # | 1st wash | 2nd wash | Washed Hair | % of Total Drug removed | 1st wash | 2nd wash | Washed Hair | % of Total Drug removed |
| | ng cocaine/10 mg hair | | | | ng cocaine/10 mg hair | | | |
| 1 | 0.7 | 0.3 | 114.5 | 0.9 | 3.2 | 1.7 | 135.7 | 3.5 |
| 2 | 3.5 | 2.8 | 65.8 | 3.7 | 8.9 | 3.2 | 81.7 | 12.9 |
| 3 | 1.3 | 0.8 | 96.5 | 2.1 | 5.8 | 2.5 | 78.7 | 9.5 |
| 4 | 2.7 | 1.7 | 173.5 | 2.5 | 2.4 | 1.9 | 191.6 | 2.2 |
| 5 | 1.1 | 1.2 | 113.1 | 2.0 | 5.4 | 2.5 | 92.1 | 7.3 |
| 6 | 0 | 0 | 135.2 | 0.0 | 1.9 | 2.1 | 118.8 | 3.3 |

Contaminated Porous and Nonporous Hair with Extended Aqueous and 90% Ethanol Washing Since the porosity of the samples in Tables 4 and 5 had not been characterized, another set of samples was permed to make the samples porous and determine whether the 90% ethanol wash would identify known contaminated porous as well as nonporous samples. Permed and unpermed samples were soaked in 1000 ng/ml of COC and METH for one hour at room temperature. Both aqueous and ethanolic washing results for COC-soaked permed and unpermed hair samples are shown in Table 7.

TABLE 7

Aqueous and 90% Ethanol Washing of Porous and Nonporous Samples soaked in 1000 ng/mL Cocaine*

| | ng/10 mg hair | | | |
|---|---|---|---|---|
| Sample # | (A) Cocaine in Hair After Washing | (B) Cocaine is Last Wash | Wash Criterion (A) − 5x(B) | Result* |
| Aqueous Buffer Washing | | | | |
| 1 | 8.8 | 1.9 | −0.9 | Negative/Contam |
| 2 | 18.2 | 7.2 | −18.1 | Negative/Contam |
| 3 | 15.4 | 3.8 | −3.8 | Negative/Contam |
| 4 | 3.0 | 0 | NA | Negative |
| 5 | 2.6 | 0.4 | NA | Negative |
| 1 Permed | 1.3 | 2.8 | NA | Negative |
| 2 Permed | 2.0 | 4.1 | NA | Negative |
| 3 Permed | 4.0 | 4.2 | NA | Negative |
| 4 Permed | 4.4 | 3.6 | NA | Negative |
| 5 Permed | 0.7 | 0.9 | NA | Negative |
| 90% Ethanol Washing | | | | |
| 1 | 15.3 | 4.8 | −8.7 | Negative/Contam |
| 2 | 18.8 | 11.6 | −39.2 | Negative/Contam |
| 3 | 21.5 | 7.9 | −18.1 | Negative/Contam |
| 4 | 5.5 | 0.9 | 1.0 | Negative/Contam |
| 5 | 3.7 | 0.7 | NA | Negative |
| 1 Permed | 103.9 | 26.7 | −29.6 | Negative/Contam |
| 2 Permed | 97.0 | 28 | −43.0 | Negative/Contam |
| 3 Permed | 68.1 | 19.8 | −30.9 | Negative/Contam |
| 4 Permed | 71.8 | 14.0 | 1.8 | Negative/Contam |
| 5 Permed | 21.6 | 6.5 | −10.9 | Negative/Contam |

*Total Cocaine on unpermed hair ranged from 10.2-91.9 ng/10 mg hair; total cocaine on permed hair ranged from 73.9-221.1 ng/10 mg hair. Cutoff for cocaine in hair is 5 ng/10 mg hair.

The total COC in the unpermed samples ranged from 10.2 to 91.9 ng/10 mg hair; in the permed samples, the total COC taken up by the hair was 73.9-221.1 ng/10 mg hair. Although, as expected, the uptake in the permed samples was greater than in the unpermed, both permed and unpermed samples were either negative after washing (under cutoff) or failed the wash criterion, indicating contamination. It is generally the case with contamination of porous samples that "what goes in easily also comes out easily." Prior cosmetic histories of the ponytails received from the salons was not known, so it is possible some of the hair that we permed may already have had some prior treatment to cause some porosity, accounting for the wide range of uptake among the unpermed samples. Also, older hair from ponytails is often porous due to mechanical damage over time (For in vitro experimenters, this is a note of caution that ponytail hair may not be representative of the 0-3.9 cm proximal samples usually tested in workplace testing.) With the aqueous buffer washing, 3 unpermed samples were above the cutoff after washing and were identified as negative or contaminated by application of the wash criterion. Two unpermed and all of the permed samples were negative by the cutoff after washing and did not require application of the wash criterion. With ethanolic washing, one unpermed sample fell below the cutoff, and 4 unpermed and all 5 permed samples fell above the cutoff but were identified as negative or contaminated after application of the wash criterion, thus demonstrating the effectiveness of the 90% ethanol wash and use of the wash criterion with this wash solvent to identify COC contamination.

With the METH-soaked samples, the range of METH taken up by the unpermed hair samples was 4.6-66.0 ng/10 mg hair (average=26), and for the permed samples was 33.3 to 95.6 ng/10 mg hair (average=52) (Table 8). All except one unpermed sample fell below the cutoff after aqueous washing, and one fell above the cutoff and was identified as contaminated/negative by the wash criterion. After ethanolic washing, three unpermed samples fell below the cutoff after washing and the remainder of the samples were identified as contaminated/negative by the wash criterion. Also, none of these samples contained the metabolite (AMP). This supports the conclusion that the ethanolic washing and wash criterion identifies contamination for both intact and porous hair.

TABLE 8

Aqueous and 90% Ethanol Washing of Nonporous and Porous Hair Samples soaked in 1000 ng/mL Methamphetamine*

| | ng/10 mg hair | | | |
|---|---|---|---|---|
| Sample # | (A) Meth in Hair After Washing | (B) Meth in Last Wash | Wash Criterion (A) − 3.5x(B) | Result* |
| Aqueous Buffer Washing | | | | |
| 1 | 0 | 0 | NA | Negative |
| 2 | 1.3 | 0.5 | NA | Negative |
| 3 | 8.8 | 4.6 | −7.3 | Negative/Contam |
| 4 | 1.4 | 0.8 | NA | Negative |
| 5 | 0 | 0 | NA | Negative |
| 1 Permed | 0 | 0 | NA | Negative |
| 2 Permed | 0 | 0 | NA | Negative |
| 3 Permed | 0 | 0 | NA | Negative |
| 4 Permed | 0 | 0 | NA | Negative |
| 5 Permed | 0 | 0 | NA | Negative |
| 90% Ethanol Washing | | | | |
| 1 | 4.5 | 3.0 | NA | Negative |
| 2 | 7.3 | 0.9 | 0.7 | Negative/Contam |
| 3 | 5.0 | 8.6 | −25.1 | Negative/Contam |
| 4 | 4.2 | 0.4 | NA | Negative |
| 5 | 3.7 | 4.9 | NA | Negative |
| 1 Permed | 16.1 | 5.3 | −2.5 | Negative/Contam |
| 2 Permed | 17.6 | 6.5 | −5.2 | Negative/Contam |
| 3 Permed | 29.1 | 7.9 | 1.5 | Negative/Contam |
| 4 Permed | 26.2 | 8.4 | −3.2 | Negative/Contam |
| 5 Permed | 5.5 | 3.5 | −6.8 | Negative/Contam |

*Total Meth on unpermed hair ranged from 4.6-66.0 ng/10 mg hair (average = 26); total meth on permed hair ranged from 33.3-95.6 ng/10 mg hair (average = 52). Cutoff for methamphetamine is 5 ng/10 mg hair Washing Studies on Cocaine and Methamphetamine-Positive Hair Samples Cocaine A demonstration of ethanolic washing for previously identified COC-positive hair compared aqueous washing of positive COC hair samples with ethanolic washing (Table 9). These samples did not fail the wash criterion using the aqueous solvent, and the intent was to assess differences in results with aqueous vs ethanolic washing. With these samples, which were only moderately porous or nonporous (Integrity Values of 5-7), both methods produced essentially similar results, and all samples were positive by both methods, passing the wash criterion, with COC above the cutoff and BE>5% of COC.

TABLE 9

Aqueous and 90% Ethanol Washing of Moderately and Minimailly Porous hair

| Sample | Integrity Value | Wash Type | Washes Hair Results | | | Washing Resltus | | |
|---|---|---|---|---|---|---|---|---|
| | | | COC ng/10 mg hair | BE | % BE | Last Wash (ng COC/10 mg hair) | Wash Criterion* | Pass/Fail |
| 1 | 5 | Ethanolic | 25.6 | 1.4 | 5.5 | 1.8 | 16.6 | P |
| | | Aqueous | 24.5 | 1.3 | 5.3 | 1.0 | 19.5 | P |
| 2 | 6 | Ethanolic | 587.9 | 92.9 | 15.8 | 47.2 | 351.9 | P |
| | | Aqueous | 628.7 | 80.7 | 12.8 | 32.4 | 466.7 | P |
| 3 | 7 | Ethanolic | 33.4 | 1.3 | 5.7 | 1.3 | 26.9 | P |
| | | Aqueous | 34.1 | 1.7 | 5.0 | 3.3 | 17.6 | P |
| 4 | 7 | Ethanolic | 1274.3 | 161.2 | 12.7 | 107.1 | 738.8 | P |
| | | Aqueous | 1386.7 | 222.5 | 16.0 | 70.1 | 1036.2 | P |
| 5 | 6 | Ethanolic | 38.2 | 3.5 | 9.2 | 0.7 | 34.7 | P |
| | | Aqueous | 34.8 | 2.3 | 6.6 | 0 | 34.8 | P |
| 6 | 7 | Ethanolic | 23.3 | 5.3 | 22.7 | 0 | 23.3 | P |
| | | Aqueous | 33.4 | 5.5 | 16.5 | 0 | 33.4 | P |
| 7 | 6 | Ethanolic | 12.8 | 1.3 | 10.2 | 0 | 12.8 | P |
| | | Aqueous | 15.6 | 1.4 | 9.0 | 0 | 15.6 | P |

Next, fourteen hair samples with aqueous wash results suggesting contamination or porosity were tested by the digestion-rate integrity test, with results showing moderate damage or porosity (Integrity Values of 4-6), and one relaxed sample (Table 10). These samples were then washed with the 90% ethanol wash. Results of the aqueous and ethanolic washes and application of the wash criterion in each case are shown in Table 7. In all of the cases in the table, the samples passed the wash criterion after ethanolic washing, and were positive with COC above the cutoff and BE>5% of COC. In some cases (e.g., #3, 4, 5, 6, 11), the aqueous wash appeared to preferentially extract BE, as suggested by the lower BE in the aqueous washed sample.

TABLE 10

Aqueous and 90% Ethanol Washing of Porous Cocaine-Containing Hair

| Sample | Integrity Value | Wash Type | Washed Hair Results | | | Washing Results | | |
|---|---|---|---|---|---|---|---|---|
| | | | COC ng/10 mg hair | BE | % BE | Last Wash (ng COC/10 mg hair) | Wash Criterion* | Pass/Fail |
| 1 | 6 | Ethanolic | 106.7 | 16.7 | 15.7 | 3.6 | 88.7 | P |
| | | Aqueous | 61 | 9.8 | 16.1 | 26.5 | −71.5 | F |
| 2 | 5 | Ethanolic | 97 | 8.5 | 8.8 | 5.3 | 70.5 | P |
| | | Aqueous | 106.9 | 8.3 | 7.8 | 29.8 | −42.1 | F |
| 3 | 5 | Ethanolic | 30.8 | 5.7 | 18.5 | 3.5 | 13.3 | P |
| | | Aqueous | 21.6 | 2.8 | 13.0 | 6.8 | −9.9 | F |
| 4 | 5 | Ethanolic | 99.6 | 8.6 | 8.6 | 15.1 | 24.1 | P |
| | | Aqueous | 76.6 | 2 | 2.6 | 17.7 | −11.9 | F |
| 5 | 6 | Ethanolic | 27.3 | 5.9 | 21.6 | 1.1 | 21.8 | P |
| | | Aqueous | 26.6 | 4.3 | 16.2 | 5.2 | 0.6 | F |
| 6 | 5 | Ethanolic | 34.1 | 12.2 | 35.8 | 2 | 24.1 | P |
| | | Aqueous | 38 | 9.3 | 24.5 | 12.9 | −26.5 | F |
| 7 | 5 | Ethanolic | 600.9 | 61.3 | 10.2 | 46.2 | 369.9 | P |
| | | Aqueous | 368.6 | 62.1 | 16.8 | 81.3 | −37.9 | F |
| 8 | 4 | Ethanolic | 155.4 | 32.0 | 20.5 | 23.3 | 38.9 | P |
| | | Aqueous | 158.5 | 28.1 | 17.7 | 38.2 | −32.5 | F |
| 9 | 6 | Ethanolic | 12.6 | 2.4 | 19.0 | 1.1 | 7.1 | P |
| | | Aqueous | 21.8 | 3.5 | 16.0 | 20 | −78.2 | F |
| 10 | 6 | Ethanolic | 11.6 | 2.6 | 22.4 | 1.4 | 5.1 | P |
| | | Aqueous | 18.6 | 4.5 | 24.1 | 9.8 | −30.4 | F |
| 11 | 5 | Ethanolic | 13.9 | 3.5 | 25.1 | 1.3 | 7.4 | P |
| | | Aqueous | 10.8 | 2.2 | 20.3 | 2.1 | 0.3 | F |
| 12 | 5 | Ethanolic | 14.2 | 0.8 | 5.6 | 1.5 | 6.7 | P |
| | | Aqueous | 11.1 | 0.7 | 6.3 | 2.7 | −2.4 | F |
| 13 | Relaxed | Ethanolic | 616.7 | 40.7 | 6.6 | 76.8 | 232.7 | P |
| | | Aqueous | 736.0 | 41.0 | 5.6 | 382.8 | −1178 | F |
| 14 | 6 | Ethanolic | 12.2 | 2.2 | 18.0 | 0.9 | 7.7 | P |
| | | Aqueous | 11.3 | 1.8 | 15.9 | 3.0 | −3.7 | F |

Table 11 shows samples that failed the wash criterion for contamination after washing with either aqueous or ethanolic solvents. These samples are not reported positive; they may be reported as follows: "The hair sample submitted is an unsuitable specimen that appears to be heavily contaminated with drug beyond that which can be removed or accounted for."

TABLE 11

Cocaine-containing samples falling both Aqueous and 90% Ethanol Washing and not reported as positive

| Sample | Integrity Value | Wash Type | Washed Hair Result | | | Washing Results | | Pass/Fail |
| | | | COC ng/10 mg hair | BE | % BE | Last Wash (ng COC/10 mg hair) | Wash Criterion* | |
| --- | --- | --- | --- | --- | --- | --- | --- | --- |
| 1 | 4 | Ethanolic | 25 | 2.7 | 10.8 | 4.9 | 0.5 | F |
| | | Aqueous | 30.2 | 0.9 | 3.0 | 14.5 | −57.7 | F |
| 2 | Relaxed | Ethanolic | 24.2 | 2.5 | 10.3 | 51.1 | −231.3 | F |
| | | Aqueous | 17.8 | 0.6 | 3.4 | 62.9 | −296.7 | F |
| 3 | 6 | Ethanolic | 17.4 | 1.8 | 10.3 | 4.3 | −4.1 | F |
| | | Aqueous | 14.7 | 1.2 | 8.2 | 4.3 | −6.8 | F |
| 4 | Relaxed | Ethanolic | 29.5 | 1.6 | 5.4 | 8.1 | −1.1 | F |
| | | Aqueous | 30.5 | 0.6 | 2.0 | 45.4 | −196.5 | F |
| 5 | 7 | Ethanolic | 84.2 | 26.1 | 31.0 | 54.2 | −186.8 | F |
| | | Aqueous | 273.0 | 41 | 15.0 | 267.6 | −1065 | F |
| 6 | 8 | Ethanolic | 49.6 | 3.8 | 7.7 | 25 | −75.4 | F |
| | | Aqueous | 60.2 | 3.3 | 5.5 | 15 | −14.8 | F |
| 7 | 8 | Ethanolic | 15.9 | 4.0 | 25.2 | 10.6 | −37.1 | F |
| | | Aqueous | 18.1 | 4.3 | 23.8 | 8.3 | −23.4 | F |
| 8 | 4 | Ethanolic | 19.9 | 2.1 | 10.6 | 4.6 | −3.1 | F |
| | | Aqueous | 22.0 | 2.3 | 10.5 | 8.9 | −22.5 | F |

Methamphetamine

Some moderately porous samples that previously tested positive for METH after aqueous washing were tested for integrity and washed with the ethanolic method (Table 12). The aqueous-washed hair had lower METH values in the case of #s 1 and 5, but all samples were positive by both the aqueous and ethanolic wash methods. This supports the validity of washing with the ethanolic method.

TABLE 12

Aqueous and 90% Ethanol Washing of Moderately Porous Methamaphetamine-Positive Hair

| Sample # | Integrity Value | Wash Method | Hair after Washing | | | Wash Content | | | Wash Criterion | WC Pass/Fail |
| | | | METH ng/10 mg hair | AMP | % AMP | METH ng/10 mg hair | AMP | % AMP | | |
| --- | --- | --- | --- | --- | --- | --- | --- | --- | --- | --- |
| 1 | 4 | Ethanol | 110.4 | 8.7 | 7.9 | 2.9 | 0.2 | NA | 100.3 | P |
| | | Aqueous | 70.8 | 4.9 | 6.9 | 14.9 | 1.7 | 11.4 | 18.7 | P |
| 2 | 6 | Ethanol | 68.3 | 4.1 | 6.0 | 2.3 | 0.1 | NA | 60.3 | P |
| | | Aqueous | 78 | 4.5 | 5.8 | 7.6 | 0.5 | 6.6 | 51.4 | P |
| 3 | 5 | Ethanol | 157.2 | 19.8 | 12.6 | 3.2 | 0.3 | 9.4 | 146.0 | P |
| | | Aqueous | 154.6 | 16.9 | 10.9 | 28.9 | 4.2 | 14.5 | 53.5 | P |
| 4 | 6 | Ethanol | 88.9 | 4.6 | 5.2 | 0.3 | 0 | NA | 67.9 | P |
| | | Aqueous | 65.1 | 2.8 | 43 | 5.5 | 0.3 | 5.5 | 45.9 | P |
| 5 | 5 | Ethanol | 142.1 | 9.4 | 6.6 | 4.7 | 0.3 | 6.4 | 125.7 | P |
| | | Aqueous | 115.5 | 7.3 | 6.3 | 14.5 | 1.3 | 9.0 | 64.8 | P |

Another 20 twenty samples were tested for integrity when the aqueous wash criterion result indicated either contamination or porosity. The results of aqueous and ethanolic washing, shown in Table 13, show that in all these cases of increased porosity the ethanolic washing produced an acceptable Wash Criterion. Comparing results of ethanolic washing versus aqueous washing can show a variety of effects in amounts of drug in the washes and amounts remaining in hair. This is likely due to combined effects of true contamination, porosity and amount of ingested dose.

TABLE 13

Aqueous and 90% Ethanol Washing of Methamphetamine-Containing Hair Samples

| | | | Washing Results | | | | | |
|---|---|---|---|---|---|---|---|---|
| | | | Hair after Washing | | | | | Wash |
| Sample # | Intergrity Value | Wash Method | METH ng/10 mg hair | AMP | % AMP | Last Wash ng METH/10 mg hair | Wash Criterion | Wash Criterion Pass/Fail |
| 1 | 3 | Ethanolic | 16.8 | 0.5 | 3.0 | 2 | 9.8 | P |
| | | Aqueous | 16.5 | 0.4 | 2.4 | 3.4 | 4.6 | F |
| 2 | 4 | Ethanolic | 10.4 | 0.8 | 7.7 | 0.5 | 8.65 | P |
| | | Aqueous | 6.6 | 3.5 | 7.4 | 1.2 | 2.6 | F |
| 3 | 4 | Ethanolic | 18.5 | 1.4 | 10.4 | 0.5 | 11.75 | P |
| | | Aqueous | 9.6 | 1.1 | 11.5 | 5.8 | −10.7 | F |
| 4 | 5 | Ethanolic | 6.8 | 0.5 | 7.4 | 0 | 6.8 | P |
| | | Aqueous | 7.5 | 0.5 | 6.7 | 2.5 | −1.25 | F |
| 5 | 5 | Ethanolic | 8.5 | 0.5 | 5.9 | 0.4 | 7.1 | P |
| | | Aqueous | 8.2 | 3.5 | 6.1 | 1.3 | 3.65 | F |
| 6 | 6 | Ethanolic | 10.6 | 1 | 9.4 | 0.9 | 7.45 | P |
| | | Aqueous | 6.4 | 0.5 | 7.8 | 0.8 | 3.6 | F |
| 7 | 6 | Ethanolic | 39.9 | 7.2 | 18.0 | 4.6 | 23.8 | P |
| | | Aqueous | 34.9 | 6 | 17.2 | 11.5 | −5.35 | F |
| 8 | 6 | Ethanolic | 14.9 | 2.7 | 18.1 | 0.9 | 11.75 | P |
| | | Aqueous | 9.4 | 1.4 | 14.9 | 3.3 | −2.15 | F |
| 9 | 4 | Ethanolic | 83.2 | 6.6 | 7.9 | 4 | 69.2 | P |
| | | Aqueous | 24.1 | 1.6 | 6.6 | 11.8 | −17.2 | F |
| 10 | 6 | Ethanolic | 19.5 | 1 | 5.1 | 1.4 | 14.6 | P |
| | | Aqueous | 8.4 | 0.6 | 7.1 | 3.1 | −2.45 | F |
| 11 | 6 | Ethanolic | 32.6 | 2.8 | 8.6 | 3.7 | 19.65 | P |
| | | Aqueous | 26.2 | 2 | 7.6 | 7.2 | 1 | F |
| 12 | 4 | Ethanolic | 10.5 | 1.3 | 12.4 | 0.4 | 9.1 | P |
| | | Aqueous | 5.7 | 0.36 | 6.3 | 2 | −1.3 | F |
| 13 | 5 | Ethanolic | 9.5 | 0.6 | 6.3 | 0 | 9.5 | P |
| | | Aqueous | 7.5 | 0.5 | 6.7 | 1.6 | 1.9 | F |
| 14 | 4 | Ethanolic | 6.7 | 0.9 | 13.4 | 0 | 6.7 | P |
| | | Aqueous | 5.3 | 0.7 | 13.2 | 1.2 | 1.1 | F |
| 15 | 4 | Ethanolic | 62.9 | 3.1 | 4.9 | 6.3 | 40.85 | P |
| | | Aqueous | 40.9 | 1.5 | 3.7 | 12.1 | −1.45 | F |
| 16 | 4 | Ethanolic | 19.6 | 1.3 | 6.6 | 2.1 | 12.25 | P |
| | | Aqueous | 24.2 | 1.5 | 6.2 | 7.4 | −1.7 | F |
| 17 | 4 | Ethanolic | 21.8 | 3.4 | 15.6 | 2.4 | 13.4 | P |
| | | Aqueous | 19.2 | 2.9 | 15.1 | 4.5 | 3.45 | F |
| 18 | 6 | Ethanolic | 12.6 | 1.3 | 10.3 | 0.6 | 10.5 | P |
| | | Aqueous | 8.7 | 0.8 | 9.2 | 1.2 | 4.5 | F |
| 19 | 4 | Ethanolic | 19.2 | 1.3 | 6.8 | 2 | 12.2 | P |
| | | Aqueous | 8.7 | 0.6 | 6.9 | 4.3 | −6.35 | F |
| 20 | 4 | Ethanolic | 25.2 | 2.7 | 10.7 | 2.4 | 16.8 | P |
| | | Aqueous | 10.5 | 1 | 9.5 | 6.6 | −12.6 | F |

In all cases in Table 13, the presence of the metabolite amphetamine was shown, with ratios from 3.0 to 18.1% of METH in the ethanolic washed hair. The presence of AMP in the hair as a metabolite is strong evidence of METH ingestion. One report with controlled doses of METH stated a range in a set of 7 subjects from 7 to 37% of methamphetamine[26]. The same situation pertains here as in workplace testing for other analytes where prescription drugs can confound testing results, in which case the subject can produce proof of a prescription. In the case of METH/AMP, if a subject can demonstrate prescribed use of selegiline or amphetamine, this may affect the MRO's disposition of the findings. Also, in the case of selegiline, the metabolic products are 1-METH and 1-AMP which can be distinguished from the d forms upon request.

With porous hair, especially in the case of METH where the analyte is very readily extracted by water, the last wash is in fact a partial extraction of the hair, with the evidence for that being that the metabolite ratio in the wash is similar to that in the digest of the hair after washing. Thus, although washing is critical to determination of contamination, analysis of the wash for both the parent and its metabolite can also indicate whether drug from ingestion is entering the wash medium due to porosity of the hair. In cases of METH contamination, there should be little or no AMP present, as was seen in our in vitro contamination experiments above. In all of the results of 90% ethanol washing of 12 samples in Table 13, some of which fail the wash criterion and others pass, the amp/meth as percent of the washes was greater than 70% of that in the digested hair samples. The use of ratios of AMP in METH-containing samples and washes is an ongoing investigation that may provide an additional criterion to distinguish ingestion from contamination.

Table 13 presents more METH-containing samples, with their Integrity Values, that fail the wash criterion with both aqueous and ethanolic washing. In cases of severe porosity (Samples 1 and 2, Integrity values of 3 and 4) it is not certain whether the failed wash criterion is due to extreme porosity or contamination. Both samples were above cutoff and the AMP:METH ratios may indicate ingestion. In nonporous hair (Samples 3-8, integrity values of 6-8), the failed wash criterion signals a report of contamination. However, the presence of metabolite in these samples suggests a contaminated user.

Application of extended aqueous washing of hair has been shown to be both essential and effective in protecting against false positives due to external contamination, even in extreme laboratory simulations. The aqueous wash method described here has been validated by another laboratory as being successful in identifying contaminated samples.[29] In that exercise, a vigorous attempt to simulate a possible environmental contamination with COC included rubbing COC on hair followed by storage and 3 shampooings per week for a month. Samples were tested through-out the month-long experiment. The paper reported that using this wash procedure, all samples were identified as contaminated using a 5 ng/10 mg hair cutoff, a 0.05 BE/COC ratio, and the wash criterion. The method was again validated in a report to the U.S. Department of Justice, using similar contamination methods and the same criteria.[30] This report also found that a wash method using short exposures to non-swelling agents, in this case methanol,[31] was unsuccessful in identifying the samples as contaminated. This is consistent with the present results with COC-contaminated samples where short methanol and dichloromethane washings were inadequate to decontaminate the samples or identify them as contaminated. It should be noted as well that drug contamination is not ubiquitous in the environment, as evidenced by the fact that the great majority of samples are negative in the screening assay which is performed on unwashed samples. In fact, most samples that are contaminated are the result of users contaminating their own hair during use. On the other hand, this laboratory has reported results of clear-cut contamination, such as a case of a chest hair sample that was well above cutoff for METH but failed the wash criterion and lacked the metabolite AMP. The donor was found to be a dealer who kept drug in his shirt pocket.

Numerous reports of effects of cosmetic treatments on hair drug content have been reported, but, to date, with no method of detecting damaged hair during the analysis, leaving a gap as to the reliability of negative results, especially in light of increasing public awareness of methods for evasion of detection. Performing a search online with the words "beat hair test" produces 85,000,000 hits. Many of these are wishful thinking, but there are some that suggest excessive bleaching and re-dyeing of the hair, which can produce negative results even at the screening level, without any washing considerations. With the tests described herein, these excessively damaged samples can be detected and then re-tested for confirmation of integrity status by either the proteolytic digestion rate method or the protein assay method.

The degrees of porosity of hair samples fall on a continuum from minor mechanical damage to normal cosmetic treatments to extreme treatments, possibly with an intent to evade detection of use. If a sample is more moderately damaged, it will not be a false negative in the screening assay, but has the potential of falling below the cutoff after extensive washing, or of failing the wash criterion. The possibility of washing out drug from a damaged/porous sample does not justify eliminating washing, as washing is necessary to ensure against false positives due to external contamination as well as to remove drug deposited by sweat. Accumulation of drug from sweat on the hair of a person who does not regularly shampoo can seriously overestimate the dose and cause a light user to be above the cutoff whereas the same level of use by a subject with daily shampoo habits may fall below the cutoff. Extended washing mitigates such effects. What the occurrence of porous/damaged samples does require is a method to determine the reason for a failed wash criterion or a discrepancy between a screening result and the drug in the washed hair. In our experience, about 10% of COC-containing and 20% of METH samples fail the aqueous wash criterion, requiring an integrity test, re-washing with 90% ethanol and re-evaluation using cutoff, metabolites, and wash criterion. If a confirmation result after aqueous washing is low and inconsistent with a strong screening result, the sample needs to be subjected to an integrity test to determine the intactness/porosity of the hair. This information is then used to select a wash procedure appropriate for the state of the hair. The same applies to a sample that fails the wash criterion. A wash procedure that appears to be suitable for porous hair is the 9:1 ethanol:water washing over 3.5 hours, presented in this paper. It is suggested that the critical components of the wash procedure are the presence of enough water (or other sufficiently swelling solvent) to (1) enter the variously damaged hair samples, and (2) effect the solubilization and diffusion of the analyte out of the hair. The 90% ethanol procedure was shown to be effective in identifying in vitro contaminated porous and nonporous samples, and in identifying user samples where metabolites or prior data supported the interpretation of a positive sample due to ingested drug.

Example 5

Hair Integrity Test of Proteolytic Digests of Hair Samples: KOH Treatment

Figure 3:
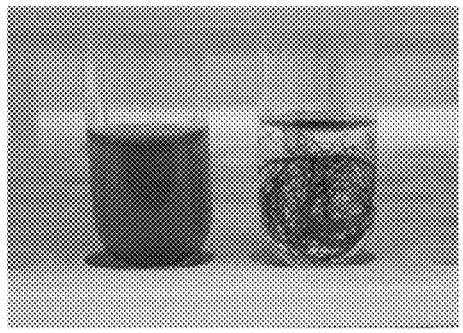
FIG. 3 is a photograph demonstrating a hair sample subjected to KOH treatment prior to treatment using a proteolytic digestion (left-hand tube) and a control sample subjected treatment using a proteolytic digestion (right-hand tube).

FIG. 3 is a photograph demonstrating a hair sample subjected to KOH treatment prior to treatment using a proteolytic digestion (left-hand tube) and a control sample subjected to treatment using a proteolytic digestion (right-hand tube). KOH-based crème application for straightening, a type of cosmetic treatment, causes hair to not dissolve, although the hair has been shown to be porous. This type of hair is identified when, at 2 hours, the control hair is well dissolved and the test hair is not dissolved (FIG. 3).

Example 6

Figure 4A:
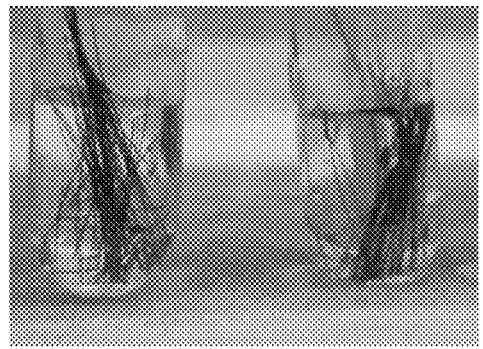
FIG. 4A is a photograph demonstrating a hair sample subjected to cellophane treatment prior to treatment using a proteolytic digestion (left-hand tube) and a control sample subjected to treatment using a proteolytic digestion (right-hand tube).
Figure 4B:
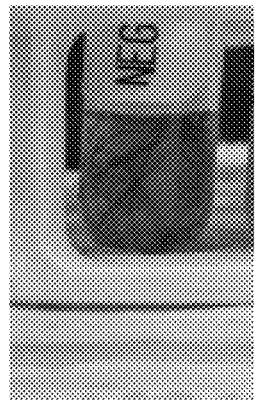
FIG. 4B is a photograph demonstrating a hair sample subjected to a permanent dye treatment prior to treatment using a proteolytic digestion.

Hair Integrity Test of Proteolytic Digests of Hair Samples: Cellophane Treatment FIG. 4A is a photograph demonstrating a hair sample subjected to cellophane treatment prior to treatment using a proteolytic digestion (left-hand tube) and a control sample subjected treatment using a proteolytic digestion (right-hand tube). As shown in FIG. 4A, when a hair sample treated with cellophane containing a dye is placed in the proteolytic solution, within 5 minutes dye is visible in solution but the hair may show the dissolution rate of control hair (FIG. 4A). This effect is different from permanent dye treatments where the hair has been damaged by the bleach/dye combination used for the treatment and therefore dissolves and the sample will dissolve rapidly while releasing dye (FIG. 4B).

Example 7

Non-Proteolytic $A_{380}$ for Integrity Testing

Figure 6:
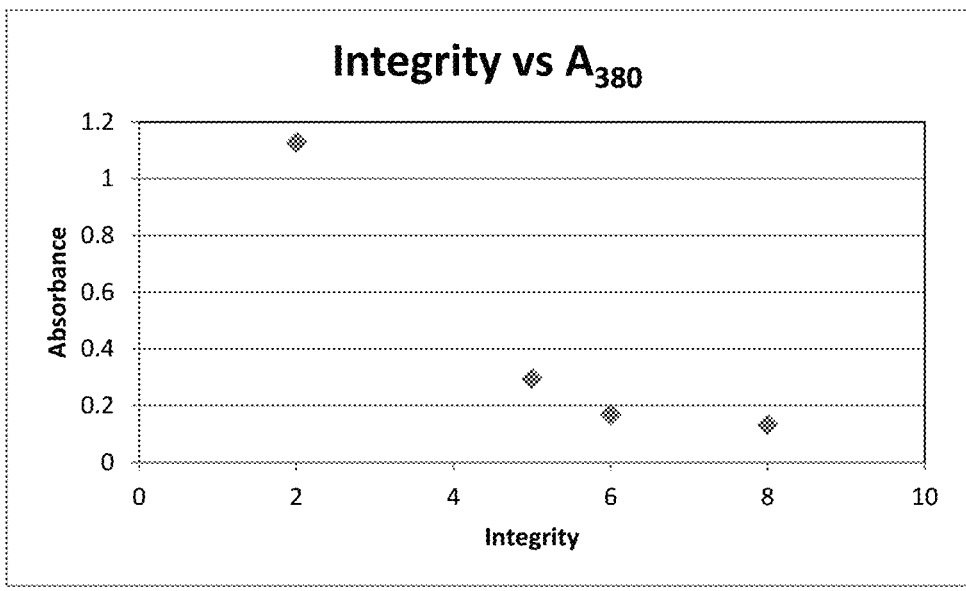
FIG. 6 is a graph demonstrating the correlation of hair integrity values (scale 1-8) verses absorbance ($A_{380}$) following non-proteolytic treatment.

Approximately 6 mg of hair was added to a plastic tube, followed by the addition of DTT digest (1.2 mL) and shaking at 37° C. for two hours. After this time period, 100 uL of the supernatant was removed from the tube and added to a 96 well microplate. 1 M HCl (10 uL) was then added to the microplate wells, followed by measuring absorbance at a wavelength of 380 nm ($A_{380}$) of the resulting solution. Results are provided in Table 14 below and FIG. 6. Invalid samples (i.e., damages hair samples) were identified by having A380>0.35.

TABLE 14

| Integrity | $A_{380}$ |
|---|---|
| 2 | 1.172 |
| 2 | 1.059 |
| 2 | 1.086 |
| 5 | 0.251 |
| 5 | 0.342 |
| 6 | 0.166 |
| 6 | 0.171 |
| 8 | 0.184 |
| 8 | 0.093 |
| 8 | 0.175 |

Example 8

Proteolytic $A_{340}$ for Integrity Testing

Figure 7:
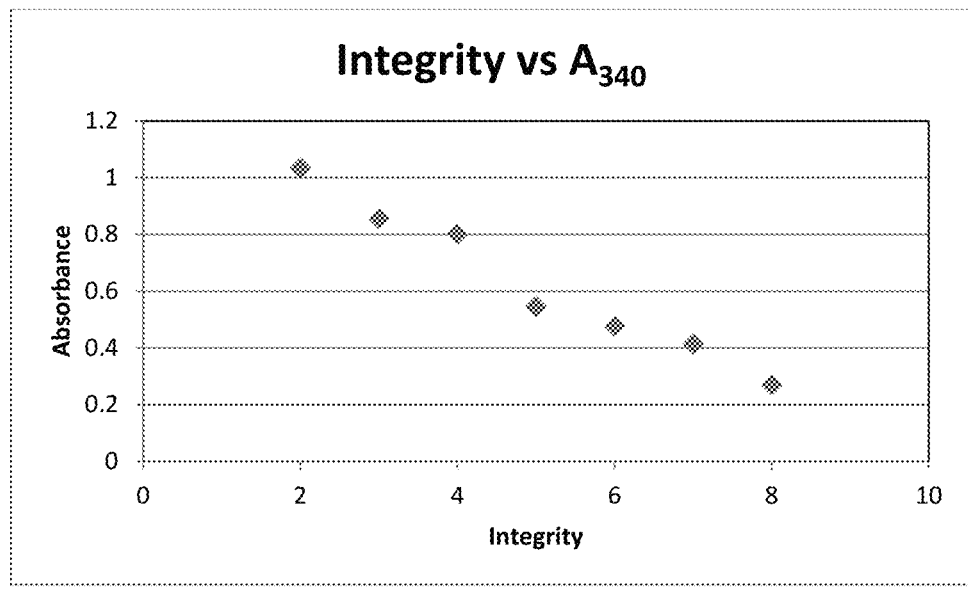
FIG. 7 is a graph demonstrating the correlation of hair integrity values (scale 1-8) verses absorbance ($A_{340}$) following protein denaturation of a test sample after proteolytic treatment.

Approximately 8 mg of hair was added to a plastic tube, followed by the addition of proteolytic digest (1.2 mL) and shaking at 37° C. After 90 minutes, 200 uL of solution was removed from the tube and added to a microplate well. 1 M HCl (10 uL) was then added to the microplate well, followed by measuring the A340 of the resulting solution. Wells with the high absorbance corresponded to samples with low integrity values. Results are provided in FIG. 7.

Example 9

Use of Proteolytic Method to Compare Samples Submitted for Follow-Up Testing

9A. Loss of Analyte Due to Excessive Hair Damage:

A first hair sample collected from a subject contained 11.9 ng/10 mg hair MDMA (ecstasy) and 0.7 ng/10 mg hair of MDA, the metabolite of MDMA. Fifteen days later, a second hair sample was collected from said subject and sent for retesting. The second hair sample contained only 0.3 ng MDMA/10 mg hair MDMA. Upon performance of the proteolytic integrity test on both samples, it was found that the first hair sample sample did not dissolve until 2 hours, indicating it was not damaged. The second hair sample dissolved completely in 30 minutes, indicating it was extremely damaged and porous. The second sample had been rendered invalid for testing, either deliberately or without knowledge of this outcome by the subject.

9B. Excess Treatments:

A first hair sample collected from a subject contained 73 ng/10 mg hair cocaine. Thirteen days later, a second hair sample was collected from said subject and sent for retesting. The second hair sample contained 0.3 ng cocaine/10 mg hair. Upon performance of the proteolytic integrity test on both samples, it was found that the first hair sample sample dissolved in 75 minutes, indicating it was somewhat damaged and porous, but not an invalid sample for testing. The second hair sample did not dissolve at all in 2 hours, indicating it had been relaxed with a potassium hydroxide cream treatment. Strong base treatment of hair renders the hair impervious to the proteolytic digestion, although drugs are still eluted from the sample. Assuming the two hair samples came from the same subject as represented, performing a strong base treatment on an already porous hair would cause it to be extremely damaged and porous such that the drug was eluted during the treatment and during subsequent regular shampooing. Results of second hair sample may be reported as invalid for testing.

9C. Loss of Analyte Due to Excessive Hair Damage).

A first hair sample collected from a subject contained 26.2 ng/10 mg hair cocaine. Seven days later, a second hair sample was collected from the individual and sent for retesting, as a follow-up retest. The second hair sample contained less than 5 ng cocaine/10 mg hair. Upon performance of the proteolytic integrity test on both samples, it was found that the original sample dissolved in 75 minutes, indicating it was somewhat damaged and porous, but not an invalid sample for testing. The second sample dissolved in 30 minutes, indicating it was a damaged and porous hair sample, causing the drug to be lost from the sample. The second hair was reported as invalid for testing.

9D.

A hair sample contained 5.3 ng morphine/10 mg hair and 5.9 ng 6-MAM/10 mg hair, indicating heroin ingestion. The sample also contained 36.2 pg carboxy-THC (C-THC, marijuana metabolite)/10 mg hair. A sample collected 9 days later contained 1.1 ng morphine/10 mg hair and 0.6 ng 6-MAM/10 mg hair, negative for heroin use as the results are below the cutoff of 2 ng/10 mg hair. The 2nd sample contained 14.8 ng C-THC. The first sample dissolved in 90 minutes (Integrity value=6) and the 2nd sample dissolved in 45 minutes (integrity value=3). Although the heroin content became negative (lost 79% of the original content due to porosity of the hair), the marijuana content was still well above the positive level of 1 pg/10 mg hair. Some analytes are more readily lost from hair than others. It has been the experience of the authors that cocaine and amphetamines are most susceptible to loss from porosity, with opiates somewhat more resistant, and marijuana most resistant to loss.

REFERENCES

[1] S. Tanaka, R. Lio, S. Chinaka, N. Takayama, K. Hayakawa. Identification of reaction products of methamphetamine and hydrogen peroxide in hair dye and decolorant treatments by high-performance liquid chromatography/mass spectrometry. *Biomedical Chromatography* 2001, 15, 45-49.

[2] S. Tanaka, R. Lio, S. Chinaka, N. Takayama, K. Hayakawa. Analysis of reaction products of cocaine and hydrogen peroxide by high-performance liquid chromatograpy/mass spectrometry. *Biomedical Chromatography* 2002, 16, 390-394.

[3] N. Takayama, S. Tanaka, R. Lio, K. Hayakawa. High-performance liquid chromatography study on effects of permanent wave, dye and decolorant treatments on methamphetamine and amphetamine in hair. *Biomedical Chromatography* 1999, 13, 257-261.

[4] S. Tanaka, R. Lio, S. Chinaka, N. Takayama, K. Hayakawa. Analysis of reaction products of morphine and codeine with hydrogen peroxide by high-performance liquid chromatograpy/mass spectrometry. *Biomedical Chromatography* 2002, 16, 390-394.

[5] C. R. Robbins. *Chemical and Physical Behavior of Hair*. Springer, New York, 2002, pp. 434-436

[6] L. F. Martins, M. Yegles, D. Thieme, R. Wennig. Influence of bleaching on the enantiomeric disposition of amphetamine-type stimulants in hair. *Forensic. Sci. Intern.* 2008, 176, 38-41

[7] M. Yegles, Y. Marson, R. Wennig. Influence of bleaching on stability of benzodiazepines in hair. *Forensic. Sci. Intern.* 2000, 107, 87-92.

[8] G. Skopp, L. Pötsch, M. R. Moeller. On cosmetically treated hair—aspects and pitfalls of interpretation. *Forensic. Sci. Intern.* 1997, 84, 43-52. ö

[9] L. Pötsch, G. Skopp. Stability of opiates in hair fibers after exposure to cosmetic treatment. *Forensic. Sci. Intern.* 1996, 81, 95-102.

[10] M. Yegles. Pitfalls in hair analysis: cosmetic treatment. *Annales de Toxicologic Analytique,* 2005, 17, 275-278.

[11] C. Jurado, P. Kintz, M. Menendez, M. Repetto. Influence of the cosmetic treatment of hair on drug testing. *Int. J. Legal Med.* 1997, 110, 159-163.

[12] C. R. Robbins. *Chemical and Physical Behavior of Hair.* Springer, New York, 2002, pp. 256-261.

[13] C. R. Robbins. *Chemical and Physical Behavior of Hair.* Springer, New York, 2002, pp. 441-446

[14] M. Schaffer, V. Hill, T. Cairns. Hair Analysis for Cocaine: The Requirement for Effective Wash Procedures and Effects of Drug Concentration and Hair Porosity in Contamination and Decontamination. *J Anal Toxicol* 2005, 29, 319-326.

[15] T. Cairns, V. Hill, M. Schaffer, W. Thistle. Amphetamines in washed hair of demonstrated users and workplace subjects. *Forensic Sci Int* 2004, 145, 137-142.

[16] T. Cairns, V. Hill, M. Schaffer, W. Thistle. Removing and identifying drug contamination in the analysis of human hair. *Forensic Sci Int* 2004, 145, 97-108.

[17] T. Cairns, V. Hill, M. Schaffer, W. Thistle. Levels of cocaine and its metabolites in washed hair of demonstrated cocaine users and workplace subjects. *Forensic Sci Int* 2004, 145, 175-181

[18] M. Schaffer, W L, Wang, J. Irving. An Evaluation of Two Wash Procedures for the Differentiation of External Contamination versus Ingestion in the Analysis of Human Hair Samples for Cocaine. *J Anal Toxicol* 2002, 26, 485-488.

[19] V. Hill, T. Cairns, M. Schaffer. Hair analysis for cocaine: Factors in laboratory contamination studies and their relevance to proficiency sample preparation and hair testing practices. *Forensic. Sci. Intern.* 2008, 176, 23-33.

[20] G. M. Roe, W. McArdle, K. Pole. 1985, The detection of cosmetic treatments on human scalp hair. Screening of forensic samples. In: Proceedings of the International Symposium on Forensic Hair Comparisons (Washington, D.C.: Government Printing Office), pp. 63-68.

[21] A. Kuzuhara. A new method of internal structural analysis of keratin fibers using Raman spectroscopy. In: *Biopolymer Research Trends,* Ed., T. S. Nemeth, 2007, Nova Science Publishers, NY, p. 61.

[22] V. Hill, M. Atefi, M. Schaffer. Non-proteolytic method for the determination of analytes in keratinized structures. U.S. Pat. No. 8,435,747, B2

[23] V. Hill, M. Atefi, M. Schaffer. Non-proteolytic method for the determination of analytes in keratinized structures. EU Patent 2,283,367.

[24] W. A. Baumgartner. Hair analysis method. U.S. Pat. No. 6,350,582.

[25] V. Hill, M. Schaffer. Integrity testing of hair samples. U.S. Patent Application No. 61/871,162.

[26] T. Inque, M. Ito, K. Kizawa. Labile proteins accumulated in damaged hair upon permanent waving and bleaching treatments. *J. Cosmet. Sci.,* 2002, 53, 337-344.

[27] Baumgartner W, Hill V. Hair analysis for drugs of abuse: forensic issues. *Proceedings of the International Symposium on Forensic Toxicology,* Federal Bureau of Investigation, Jun. 15-19, 1992, Quantico, Va., pp. 75-97.

[28] A. Polettini, E. J. Cone, D. A. Gorelick, M. A. Huestis. Incorporation of methamphetamine and amphetamine in human hair following controlled oral methamphetamine administration. *Anal. Chim. Act,* 2012, 726, 35-43.

[29] P. R. Stout, J. D. Ropero-Miller, M. R. Bayklor, J. M. Mitchell. External contamination of hair with cocaine: Evaluation of external cocaine contamination and development of performance-testing materials. *J. Anal Tox.,* 2006, 30, 490-496.

[30] J. D. Ropero-Miller, P. R. Stout. Analysis of cocaine analytes in human hair. II. Evaluation of Different Hair Color and ethnicity Types. Report to U.S. Department of Justice. Document #234628, June 2011.

[31] L. Tsanaclis, J. F. C. Wicks. Differentiation between drug use and environmental contamination when testing for drugs in hair. *Forensic Sci Int* 145, 97-108.

Other Embodiments

A number of embodiments of the invention have been described. Nevertheless, it will be understood that various modifications may be made without departing from the spirit and scope of the invention. Accordingly, other embodiments are within the scope of the following claims.

What is claimed is:

1. A method for determining the presence or absence of a drug of abuse or metabolite thereof in a hair sample of a subject comprising:
    providing a hair sample;
    contacting the hair sample with an aqueous solution comprising a reducing agent and a protease capable of digesting keratin to result in a test sample, wherein the contacting step occurs for a period of about 1 hour to about 2 hours;
    determining the amount of dissolved hair protein in the test sample using a protein assay;
    identifying the hair in the test sample as not suitable for drug analyte testing when the hair in the test sample has dissolved in the test sample more rapidly than the hair in a similarly contacted control sample; and
    if the hair in the test sample is not identified as not suitable for drug analyte testing, then
    determine if the drug of abuse or metabolite thereof is present or absent in the hair sample.

2. The method of claim 1, wherein the protease is selected from the group consisting of papain, chymopapain, and proteinase K.

3. The method of claim 1, further comprising assessing the condition of the hair in the test sample by visual inspection at predetermined time intervals.

4. The method of claim 1, wherein the reducing agent is selected from the group consisting of 2,3 dihydroxybutane-1,4-dithiol ("DTT"), 2,3 dihydroxybutane-1,4-dithiol ("DTE"), thioglycolate, cysteine, sulfites, bisulfites, sulfides, bisulfides, tris(2-carboxyethyl)phosphine ("TCEP"), and mixtures thereof.

5. The method of claim 1, wherein the aqueous solution comprises 0.1%, 0.2%, 0.3%, 0.4%, 0.5%, 0.6%, 0.7%, 0.8%, 0.9% or 1.0% of the reducing agent.

6. The method of claim 1, wherein the pH at which the contacting step is performed is between about 7.0 and 10.5, between about 8.8 and 10.5, between about 8.8 and 9.7, between about 8.8 and 9.5, or between about 9.4 and 9.7.

7. The method of claim 1, wherein the temperature at which the contacting step or the determining step is performed is between about 20° C. and about 40° C.

8. The method of claim 1, wherein determining the amount of dissolved hair protein in the test sample occurs at about 15 minute intervals.

9. The method of claim 3, wherein the predetermined time intervals are about 15 minute intervals.

10. The method of claim 1, wherein the step of determining the amount of dissolved hair protein in the test sample is completed using a portion of the hair sample; and determining the presence or absence of a drug of abuse or metabolite thereof is completed using: (a) the same portion of the hair sample; or (b) another portion of the hair sample.

11. The method of claim 1, further comprising identifying the hair sample as being previously treated with potassium hydroxide if the hair sample fails to dissolve after a time period of about 120 minutes.

12. The method of claim 1, further comprising identifying the hair sample as being previously treated with a cellophane hair treatment if a dye is visible in the test solution within about 5 minutes of contacting the hair sample with an aqueous solution comprising a reducing agent and a protease.

13. The method of claim 1, wherein the hair sample is a washed hair sample.

14. The method of claim 1, wherein the amount of dissolved hair protein the test sample is determined using a protein assay selected from the group consisting of the Lowry Assay or the Bradford Assay.

15. The method of claim 1, further comprising indicating the hair sample as unsuitable for determining if an analyte is present in the test solution if the hair sample has been identified as damaged.

16. The method of claim 1, wherein determining the presence or absence of a drug of abuse or a metabolite thereof comprises an enzyme immunoassay specific for the analyte, a mass spectrometry technique, or a chromatographic technique.

17. The method of claim 1, wherein the drug of abuse or metabolite thereof is selected from the group consisting of a prescription medicine or metabolite thereof, a pain medication or metabolite thereof, a nutrient, and an endogenous analyte, or a salt form of any of the foregoing.

18. The method of claim 17, wherein the drug of abuse or metabolite thereof is selected from the group consisting of cocaine, benzoylecgonine, cocaethylene, norcocaine, phencyclidine (PCP), amphetamine, methamphetamine, cannabinoid, THC, carboxy-THC, heroin, codeine, morphine, 6-monoacetylmorphine (MAM), oxycodone, 3,4-methylenedioxyamphetamine (MDA) and 3,4-methylenedioxymethamphetamine (MDMA).

19. The method of claim 17, wherein the prescription medicine or metabolite thereof, or pain medication or metabolite thereof is an opioid, cannabinoid, nonsteroid anti-inflammatory drugs (NSAID), steroid, amphetamine, benzodiazepine, barbiturate, tricyclic, or ephedrine, or metabolite thereof.

20. The method of claim 1, further comprising determining the amount of the analyte in the test solution.

21. The method of claim 1, wherein determining the amount of dissolved hair protein in the test sample occurs at 0, 15, 30, 45, 60, 75, 90 and 120 minutes after contacting the hair sample with an aqueous solution comprising a reducing agent and a protease capable of digesting keratin.

22. The method of claim 1, further comprising identifying the hair sample as suitable for further processing if the rate of dissolution in the test solution is commensurate with the rate of dissolution in the control sample.

23. The method of claim 1, further comprising determining the rate of dissolution of the hair in the test sample using a protein assay; and identifying the hair in the test sample as not suitable for drug analyte testing when the hair in the test sample has dissolved in the test sample more rapidly than the hair in a similarly contacted control sample.

24. A method for determining the presence or absence of a drug of abuse or metabolite thereof in a hair sample of a subject comprising:
    providing a hair sample;
    contacting the hair sample with an aqueous solution comprising a reducing agent and a protease capable of digesting keratin to result in a test sample, wherein the contacting step occurs for a period of about 1 hour to about 2 hours;
    determining the rate of dissolution of the hair in the test sample using a protein assay; and
    identifying the hair in the test sample as not suitable for drug analyte testing when the hair in the test sample has dissolved in the test sample more rapidly than the hair in a similarly contacted control sample; and
    if the hair in the test sample is not identified as not suitable for drug analyte testing, then
    determine if the drug of abuse or metabolite thereof is present or absent in the hair sample.

* * * * *